(12) United States Patent
Weissman et al.

(10) Patent No.: US 12,054,734 B2
(45) Date of Patent: Aug. 6, 2024

(54) PURIFICATION AND PURITY ASSESSMENT OF RNA MOLECULES SYNTHESIZED WITH MODIFIED NUCLEOSIDES

(71) Applicant: The Trustees of the University of Pennsylvania, Philadelphia, PA (US)

(72) Inventors: Drew Weissman, Wynnewood, PA (US); Katalin Kariko, Rydal, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 464 days.

(21) Appl. No.: 17/338,795

(22) Filed: Jun. 4, 2021

(65) Prior Publication Data

US 2021/0292786 A1    Sep. 23, 2021

Related U.S. Application Data

(60) Division of application No. 15/664,036, filed on Jul. 31, 2017, now Pat. No. 11,060,107, which is a continuation of application No. 14/776,525, filed as application No. PCT/US2014/026140 on Mar. 13, 2014, now abandoned.

(60) Provisional application No. 61/783,645, filed on Mar. 14, 2013.

(51) Int. Cl.
| | |
|---|---|
| *C12N 15/85* | (2006.01) |
| *C07H 21/02* | (2006.01) |
| *C07K 14/475* | (2006.01) |
| *C07K 14/505* | (2006.01) |
| *C07K 14/52* | (2006.01) |
| *C12P 19/34* | (2006.01) |
| *A61K 48/00* | (2006.01) |

(52) U.S. Cl.
CPC ............. *C12N 15/85* (2013.01); *C07H 21/02* (2013.01); *C07K 14/475* (2013.01); *C07K 14/505* (2013.01); *C07K 14/52* (2013.01); *C12P 19/34* (2013.01); *A61K 48/00* (2013.01); *C12N 2310/335* (2013.01); *C12N 2320/30* (2013.01)

(58) Field of Classification Search
CPC ... C12N 15/85; C12N 2310/335; C07H 21/02
See application file for complete search history.

(56) References Cited

U.S. PATENT DOCUMENTS

| | | | | |
|---|---|---|---|---|
| 8,278,036 B2* | 10/2012 | Kariko | ................. | C07K 14/505 435/375 |
| 8,808,982 B2* | 8/2014 | Dahl | ........................ | C12N 9/22 435/375 |
| 9,012,219 B2* | 4/2015 | Kariko | ................. | C12N 5/0696 435/325 |
| 9,750,824 B2* | 9/2017 | Kariko | ....................... | A61P 7/06 |
| 10,232,055 B2* | 3/2019 | Kariko | ............... | A61K 48/0075 |
| 11,060,107 B2* | 7/2021 | Weissman | ............... | C12P 19/34 |

OTHER PUBLICATIONS

Kariko (Molecular Therapy, 2008, 16:1833-1840).*
Kariko (Molecular Therapy, May 2012, 20:948-953.*
Anderson, 2010, Nucleic Acids Res, 38:5884-5892.*

* cited by examiner

*Primary Examiner* — Valarie E Bertoglio
(74) *Attorney, Agent, or Firm* — Riverside Law LLP

(57) ABSTRACT

This invention provides purified preparations of an RNA, oligoribonucleotide, or polyribonucleotide comprising a modified nucleoside, and methods of assessing purity of purified preparations of an RNA, oligoribonucleotide, or polyribonucleotide comprising a modified nucleoside.

7 Claims, 8 Drawing Sheets

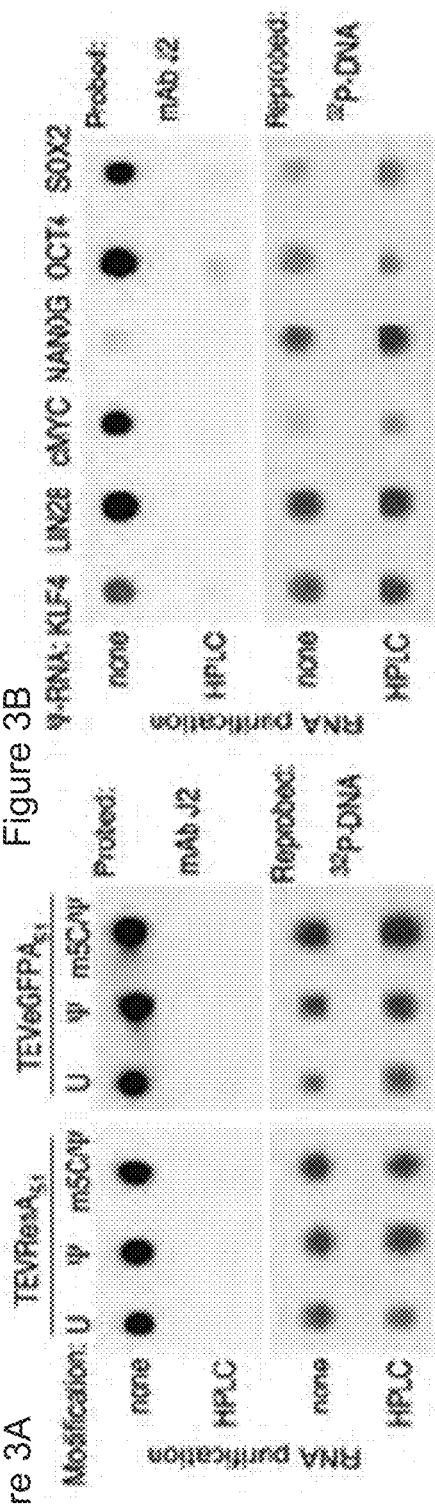
Figure 3A
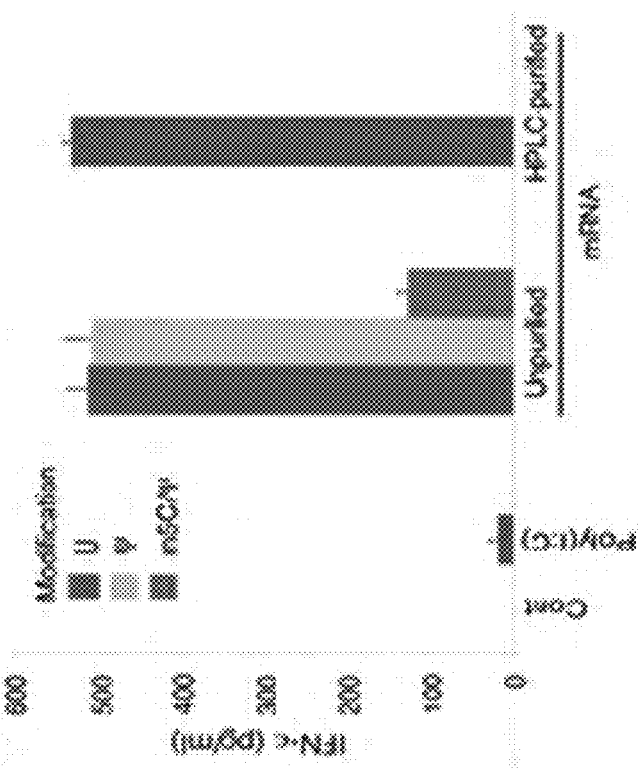
Figure 3B
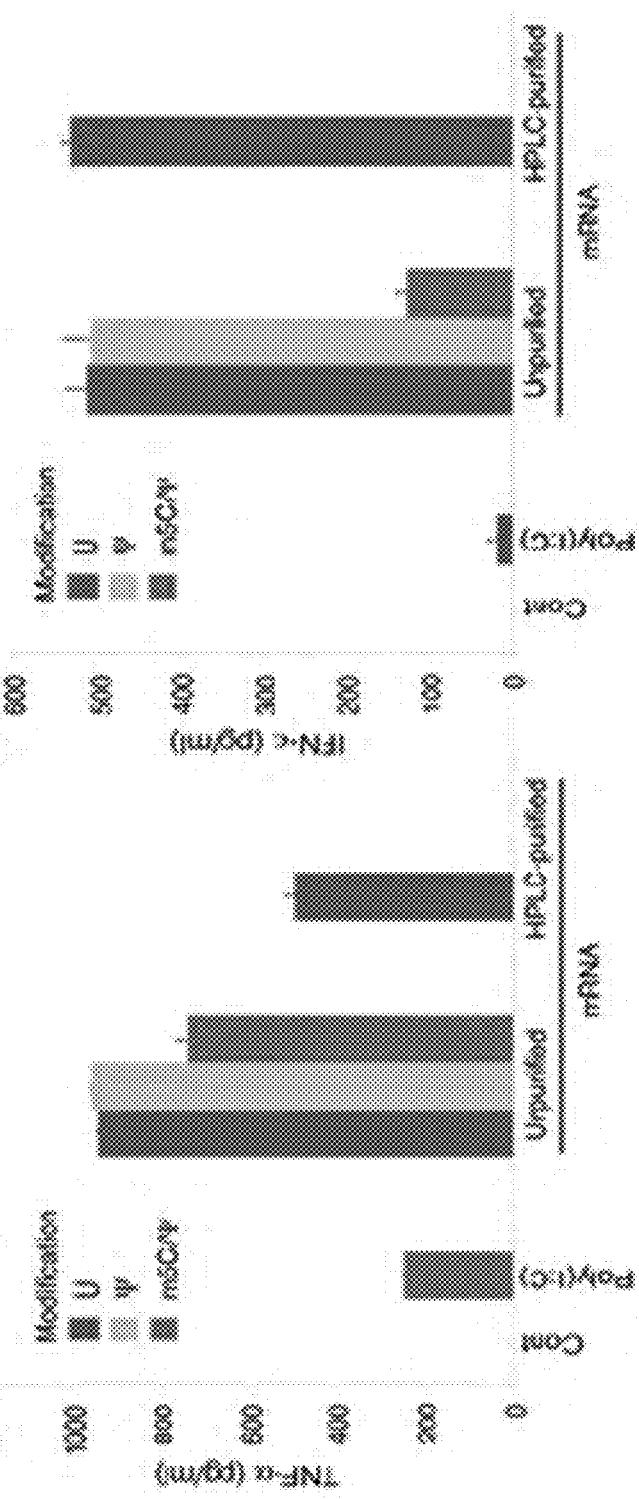
Figure 3C
Figure 3D

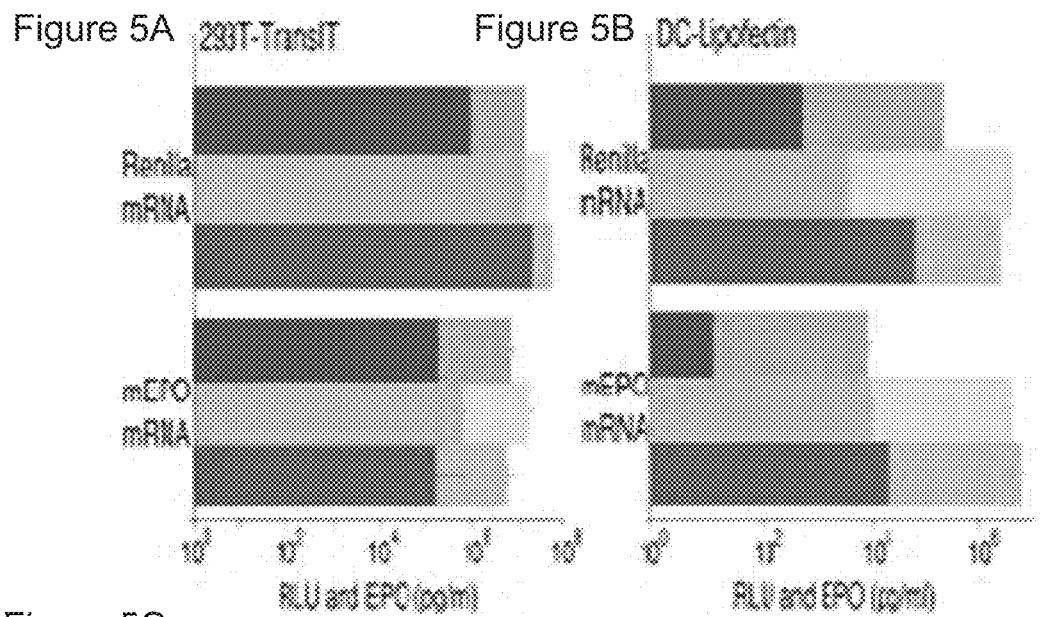
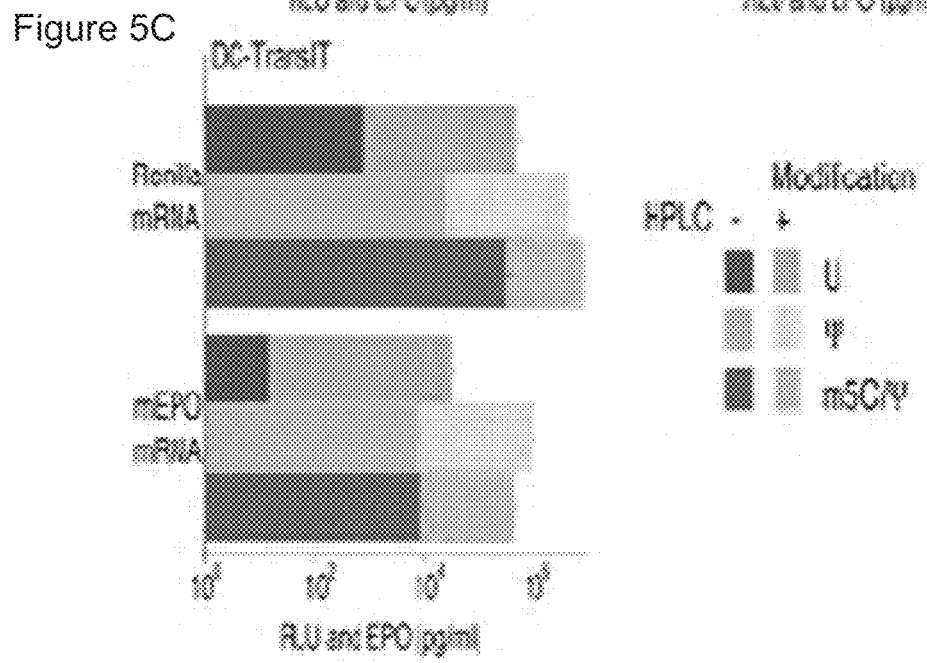
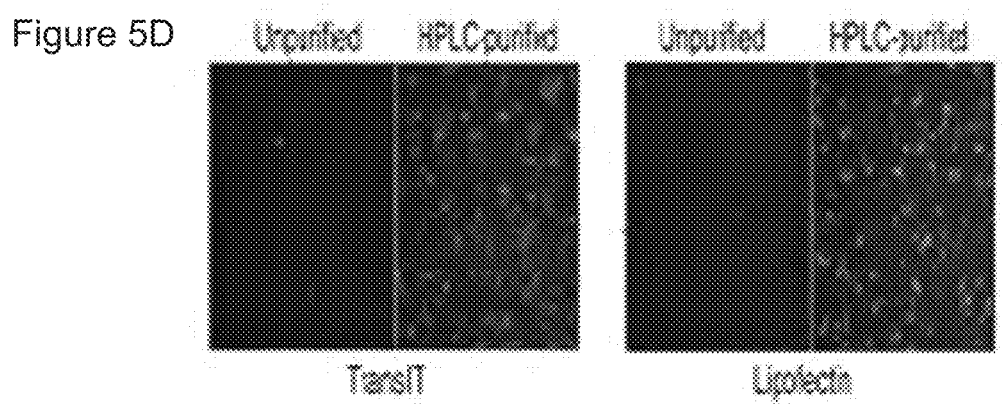

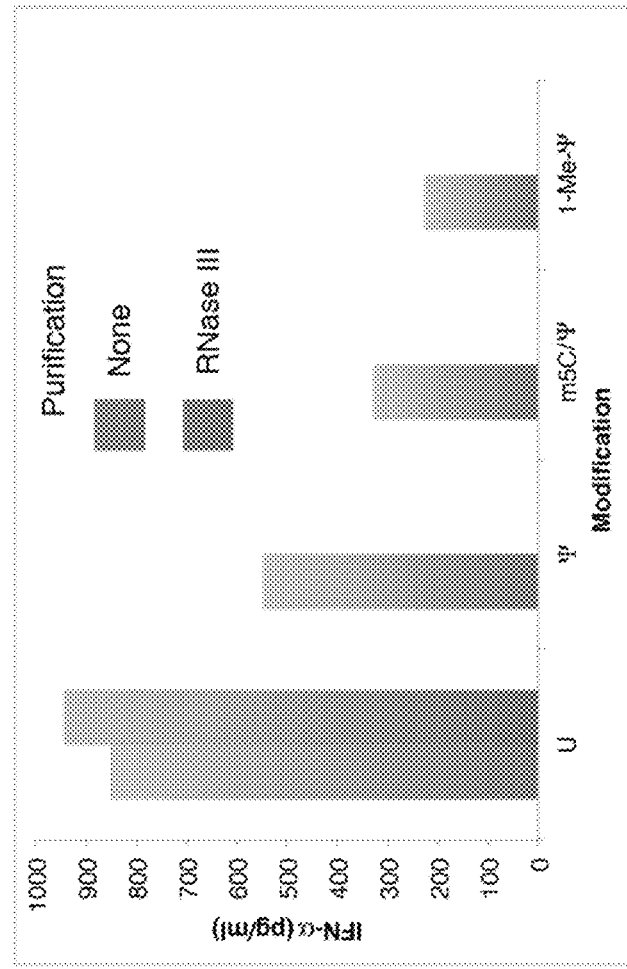
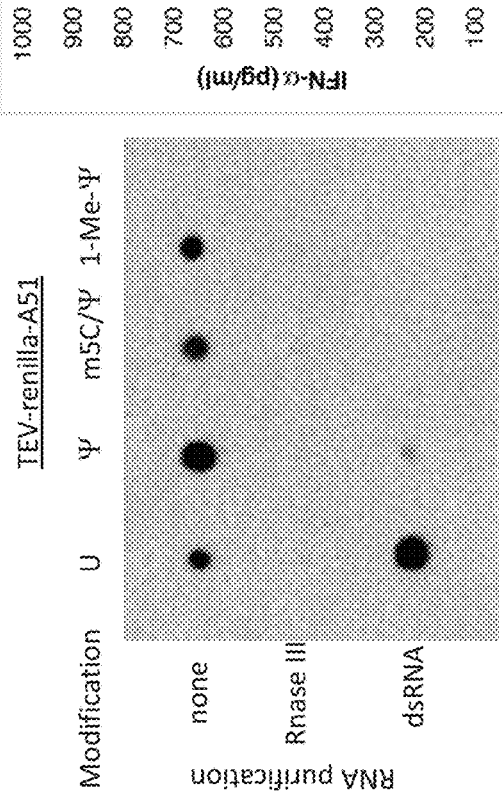
Figure 8

PURIFICATION AND PURITY ASSESSMENT OF RNA MOLECULES SYNTHESIZED WITH MODIFIED NUCLEOSIDES

CROSS-REFERENCE TO RELATED APPLICATIONS

This application is a divisional of U.S. patent application Ser. No. 15/664,036, filed Jul. 31, 2017, which is a continuation of U.S. patent application Ser. No. 14/776,525, filed Sep. 14, 2015, which is the U.S. national stage application filed under 35 U.S.C. § 371 claiming benefit to International Patent Application No. PCT/US14/26140, filed Mar. 13, 2014, which is entitled to priority under 35 U.S.C. § 119(e) to U.S. Provisional Application No. 61/783,645, filed Mar. 14, 2013, each of which is hereby incorporated by reference in its entirety.

STATEMENT REGARDING FEDERALLY SPONSORED RESEARCH OR DEVELOPMENT

This invention was made with government support under grant numbers HL087688 and AI050484, awarded by the National Institutes of Health (NIH). The government has certain rights in the invention.

BACKGROUND OF THE INVENTION

The first in vivo delivery of mRNA encoding a therapeutic protein was reported in 1992 (Jirikowski et al., Science 255:996-998), but only recently has the delivery of mRNA for scientific and therapeutic purposes gained expanded interest. Potential uses include: delivery of mRNA encoding transcription factors to generate induced pluripotent stem (iPS) cells (Angel and Yanik, 2010, PLoS One 5:e11756; Yakubov et al., 2010, Biochem Biophys Res Commun 394:189-193; Warren et al., 2010, Cell Stem Cell 7:618-630), in vivo administration to express therapeutic proteins (Jirikowski et al., Science 255:996-998; Kormann et al., 2011, Nat Biotechnol 29:154-157; Kariko et al., 2012, Mol Ther 20:948-953), ex vivo delivery to expanded cells as a cancer therapeutic (Barrett et al., 2011, Hum Gene Ther 22(12):1575-1586; Almasbak et al., 2011, Cytotherapy 13:629-640; Zhao et al., 2010, Cancer Res 70:9053-9061; Rabinovich et al., 2009, Hum Gene Ther 20:51-61; Yoon et al., 2009, Cancer Gene Ther 16:489-497), as the vector for vaccines (Kariko, et al., 2011, Nucleic Acids Res 39:e142; Kariko et al., 2008, Mol Ther 16:1833-1840; Weissman et al., 2000, J Immunol 165:4710-4717), and in vitro delivery to express protein at a high efficiency (Kariko, et al., 2011, Nucleic Acids Res 39:e142; Kariko et al., 2008, Mol Ther 16:1833-1840; Weissman et al., 2000, J Immunol 165:4710-4717).

All naturally occurring RNA is synthesized from four basic ribonucleotides ATP, CTP, UTP and GTP, but some of the incorporated nucleosides are modified post-transcriptionally in almost all types of RNA. Over one hundred different nucleoside modifications have been identified in RNA (Rozenski et al., 1999, The RNA Modification Database: 1999 update. Nucl Acids Res 27:196-197). The extent and nature of modifications vary and depend on the RNA type as well as the evolutionary level of the organism from where the RNA is derived. Ribosomal RNA, the major constituent of cellular RNA, contains significantly more nucleoside modifications in mammalian cells than bacteria. Human rRNA, for example, has 10-times more pseudouridine (Ψ) and 25-times more 2'-O-methylated nucleosides than bacterial rRNA, while rRNA from mitochondria has very few modifications. Transfer RNA (tRNA) is the most heavily modified subgroup of RNA. In mammalian tRNA, up to 25% of the nucleosides are modified, while prokaryotic tRNA contains significantly fewer modifications. Bacterial messenger RNA (mRNA) contains no nucleoside modifications, while mammalian mRNA contains modified nucleosides such as 5-methylcytidine (m5C), N6-methyladenosine (m6A), inosine and 2'-O-methylated nucleosides, in addition to N7-methylguanosine (m7G), which is part of the 5'-terminal cap. Nucleoside modifications have a great impact on the immunostimulatory potential and on the translation efficiency of RNA.

The recognition that the immunogenicity of RNA could be reduced by the incorporation of modified nucleosides with an associated increase in translation (Kariko et al., 2008, Mol Ther 16:1833-1840; Kariko et al., 2005, Immunity 23:165-175) potentially allows efficient expression of proteins in vivo and ex vivo without activation of innate immune receptors. Unfortunately, modified nucleoside-containing RNA transcribed by phage RNA polymerases still retains a low level of activation of such pathways (Warren et al., 2010, Cell Stem Cell 7(5):618-630; Kariko et al., 2008, Mol Ther 16:1833-1840; Anderson et al., 2010, Nucleic Acids Res 38:5884-5892; Kariko and Weissman, 2007, Curr Opin Drug Discov Devel 10:523-532). This remaining activation of RNA sensors could be due to modified nucleosides that do not completely suppress the RNAs ability to activate sensors (Kormann et al., 2011, Nat Biotechnol 29:154-157) or dsRNA contaminants that activate even in the presence of nucleoside modification (Kariko, et al., 2011, Nucleic Acids Res 39:e142). It is known that RNA transcribed in vitro by phage polymerase contains multiple aberrant RNAs, including short RNAs as a result of abortive transcription initiation events (Milligan et al., 1987, Nucleic Acids Res 15:8783-8798) and double stranded (ds) RNAs generated by RNA dependent RNA polymerase activity (Arnaud-Barbe et al., 1998, Nucleic Acids Res 26:3550-3554), RNA-primed transcription from RNA templates (Nacheva and Berzal-Herranz, 2003, Eur J Biochem 270:1458-1465), and self-complementary 3' extension (Triana-Alonso et al., 1995, J Biol Chem 270:6298-6307).

Thus, there is a need in the art for more purified preparations of RNA containing a reduced amount of contaminants. The present invention satisfies this need.

SUMMARY OF THE INVENTION

The invention relates to methods of preparing and assessing purified preparations of an RNA comprising a modified nucleoside. Thus, in one embodiment, the invention is a purified preparation of messenger RNA comprising a 1-methyl-pseudouridine residue. In some embodiments, the messenger RNA also comprises a poly-A tail. In some embodiments, the messenger RNA also comprises an m7GpppG cap. In some embodiments, the messenger RNA also comprises a cap-independent translational enhancer. In some embodiments, the messenger RNA comprises at least about 95% to about 99.9% of all the nucleic acid present in the purified preparation. In some embodiments, the purified preparation of messenger RNA is significantly less immunogenic than an unpurified preparation of messenger RNA with the same sequence. In some embodiments, the purified preparation of messenger RNA exhibits enhanced ability to be translated by a target cell than an unpurified preparation of messenger RNA with the same sequence. In some embodiments, the purified preparation of messenger RNA exhibits enhanced ability to be translated when delivered to a mammal than an unpurified preparation of messenger RNA with the same sequence. In some embodiments, the messenger RNA is encapsulated in a lipid nanoparticle. In some embodiments, the modified nucleoside is at least one of 1-methyl-pseudouridine and m5C. In some embodiments, the modified nucleoside is at least one of pseudouridine and m5C.

In another embodiment, the invention is a purified preparation of RNA encoding a protein of interest, where the RNA comprises at least one of a 1-methyl-pseudouridine residue and a m5C residue. In another embodiment, the invention is a purified preparation of RNA encoding a protein of interest, where the RNA comprises at least one of a pseudouridine residue and a m5C residue. In some embodiments, the messenger RNA also comprises a poly-A tail. In some embodiments, the messenger RNA also comprises an m7GpppG cap. In some embodiments, the messenger RNA also comprises a cap-independent translational enhancer. In some embodiments, the messenger RNA comprises at least about 95% to about 99.9% of all the nucleic acid present in the purified preparation. In some embodiments, the purified preparation of messenger RNA is significantly less immunogenic than an unpurified preparation of messenger RNA with the same sequence. In some embodiments, the purified preparation of messenger RNA exhibits enhanced ability to be translated by a target cell than an unpurified preparation of messenger RNA with the same sequence. In some embodiments, the purified preparation of messenger RNA exhibits enhanced ability to be translated when delivered to a mammal than an unpurified preparation of messenger RNA with the same sequence. In some embodiments, the messenger RNA is encapsulated in a lipid nanoparticle.

In one embodiment, the invention is a method of preparing a purified preparation of messenger RNA comprising at least one modified nucleoside including the steps of producing a preparation of messenger RNA comprising at least one modified nucleoside, subjecting the preparation of messenger RNA comprising at least one modified nucleoside to at least one purification process selected from the group consisting of enzyme digestion and chromatography; and isolating the purified preparation of messenger RNA comprising at least one modified nucleoside. In some embodiments, the at least one modified nucleoside is 1-methyl-pseudouridine. In some embodiments, the messenger RNA further comprises a poly-A tail. In some embodiments, the messenger RNA further comprises an m7GpppG cap. In some embodiments, the messenger RNA further comprises a cap-independent translational enhancer. In some embodiments, the messenger RNA comprises at least about 95% to about 99.9% of all the nucleic acid present in the purified preparation. In some embodiments, the messenger RNA is significantly less immunogenic than an unpurified preparation of messenger RNA with the same sequence. In some embodiments, the messenger RNA exhibits enhanced ability to be translated by a target cell than an unpurified preparation of messenger RNA with the same sequence. In some embodiments, the messenger RNA exhibits enhanced ability to be translated when delivered to a mammal than an unpurified preparation of messenger RNA with the same sequence. In some embodiments, the modified nucleoside comprises at least one of 1-methyl-pseudouridine and m5C. In some embodiments, the modified nucleoside comprises at least one of pseudouridine and m5C. In some embodiments, the preparation of messenger RNA is produced by in vitro transcription. In some embodiments, the at least one purification process is enzyme digestion. In various embodiments, the enzyme digestion is performed using at least one enzyme selected from the group consisting of RNase III, RNase V1, Dicer, and Chipper. In some embodiments, the at least one purification process is chromatography. In various embodiments, the chromatography is at least one selected from the group consisting of high performance liquid chromatography (HPLC) and fast protein liquid chromatography (FPLC).

In another embodiments, the invention is a method of inducing a mammalian cell to produce a protein of interest, the method comprising the step of contacting the mammalian cell with the purified preparation of the RNA, thereby inducing a mammalian cell to produce a protein of interest. In some embodiments, the mammalian cell is a dendritic cell. In some embodiments, the mammalian cell is an alveolar cell, an astrocyte, a microglial cell, or a neuron.

In one embodiment, the invention is a purified preparation of in vitro-transcribed RNA, comprising a 1-methyl-pseudouridine or a modified nucleoside. In some embodiments, the modified nucleoside is m5C, m5U, m6A, s2U, Ψ, or 2'-O-methyl-U. In some embodiments, the in vitro-transcribed RNA also comprises a poly-A tail. In some embodiments, the in vitro-transcribed RNA also comprises an m7GpppG cap. In some embodiments, the in vitro-transcribed RNA also comprises a cap-independent translational enhancer.

In another embodiment, the invention is a purified preparation of an in vitro-synthesized oligoribonucleotide, comprising a 1-methyl-pseudouridine or a modified nucleoside, where the modified nucleoside is m5C, m5U, m6A, s2U, Ψ, or 2'-O-methyl-U. In some embodiments, the in vitro-synthesized oligoribonucleotide is a therapeutic oligoribonucleotide.

In one embodiment, the invention is a purified preparation of a gene-therapy vector, comprising an in vitro-synthesized polyribonucleotide encoding a protein of interest, where the polyribonucleotide comprises a 1-methyl-pseudouridine or a modified nucleoside. In some embodiments, the modified nucleoside is m5C, m5U, m6A, s2U, Ψ, or 2'-O-methyl-U. In some embodiments, the polyribonucleotide further comprises a poly-A tail. In some embodiments, the polyribonucleotide further comprises an m7GpppG cap. In some embodiments, the polyribonucleotide further the comprises a cap-independent translational enhancer.

In another embodiment, the invention is a method for delivering a recombinant protein to a subject, the method comprising the step of contacting a cell of the subject with the purified preparation of the gene-therapy vector, where the cell produces the recombinant protein, thereby delivering a recombinant protein to a subject. In some embodiments, the cell is a dendritic cell. In some embodiments, the cell is a lung cell, a brain cell, or a spleen cell.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising (FIG. 1A) 200 ng of in vitro transcripts encoding mEPO and containing the indicated modified nucleosides were blotted and analyzed with K1 and J2 dsRNA-specific mAbs. The dsRNA positive control contained a 328 bp long dsRNA (25 ng). (FIG. 1B) DCs were treated with Lipofectin-complexed Renilla luciferase (T7TSRenA$_{30}$), firefly and Metridia luciferases (T7TSLucA$_{30}$, T7TSMetlucA$_{30}$), and mEPO (TEVmEPOA$_{51}$) mRNAs. TNF-α levels were measured in the supernatants at 24 h. (FIG. 1C) DCs were treated with TransIT-complexed in vitro transcripts encoding Renilla and firefly luciferases (T7TSRenA$_{30}$, T7TSLucA$_{30}$), eGFP (TE-VeGFPA$_{51}$) and mEPO (TEVmEPOA$_{51}$). IFN-α levels were measured in the supernatants at 24 h. Error bars are standard error of the mean. Data shown is from one experiment that is representative of greater than 20 experiments using many different coding sequence mRNAs.

FIG. 3, comprising FIGS. 3A-3D, depicts the results of analyses demonstrating that HPLC purification of in vitro-transcribed nucleoside modified mRNA removes dsRNA contaminants and eliminates immunogenicity. (FIG. 3A) 200 ng of RNA encoding the indicated protein and containing the indicated modified nucleosides with or without HPLC-purification were blotted and analyzed with the J2 dsRNA-specific mAb. (FIG. 3B) 200 ng of RNA encoding the indicated protein and containing Ψ-modifications with or without HPLC-purification were blotted and analyzed with the J2 dsRNA-specific mAb. Blots were reprobed with a 32P-labeled probe for the 3' UTR of the RNAs to control for amount of RNA analyzed. (FIG. 3C) DCs were treated with TEVRenA$_{51}$ RNA containing the indicated nucleoside modifications with or without HPLC purification and complexed to Lipofectin. TNF-α levels were measured in the supernatants at 24 hr. Differences in the effect of nucleoside modification on immunogenicity of Renilla encoding mRNA compared to FIG. 1B is likely due to donor variation and differences in UTRs of the RNAs. (FIG. 3D) DCs were treated with TEVLucA$_{51}$ RNA containing the indicated nucleoside modifications with or without HPLC purification and complexed to TransIT. IFN-α levels were measured in the supernatants at 24 hr. Error bars are standard error of the mean. Data shown is from one experiment that is representative of 3 or more.

FIG. 4, comprising (FIG. 4A) Heat map representing changes in expression of genes activated by RNA sensors were derived from microarray analyses of DCs treated for 6 hr with TransIT alone or transit-complexed TEVRenA$_{51}$ RNA with the indicated modifications with or without HPLC purification. RNA from medium treated cells was used as the baseline for comparison. (FIG. 4B) Northern blot of RNA from DCs treated with medium or TransIT alone or TransIT-complexed TEVRenA$_{51}$ RNA with the indicated modifications with or without HPLC purification and probed for IFN-α, IFN-β, TNF-α, and GAPDH mRNAs.

FIG. 5, comprising FIGS. 5A-5D, depicts the results of analyses demonstrating that HPLC purification of in vitro transcribed mRNA enhances translation. 293T (FIG. 5A) and human DCs (FIG. 5B-5C) were transfected with TransIT (FIG. 5A, FIG. 5C) or Lipofectin (FIG. 5B) complexed TEVRenA$_{51}$ or TEVmEPOA$_{51}$ mRNA with the indicated modifications with or without HPLC purification and analyzed for Renilla luciferase activity or levels of supernatant-associated mEPO protein at 24 hr. (FIG. 5D) Human DCs were transfected with Ψ-modified TEVeGFPA$_n$ mRNA with or without HPLC purification (0.1 μg/well) complexed with Lipofectin or TransIT and analyzed 24 hr later. Error bars are standard error of the mean. Data shown is from one experiment that is representative of 3 or more.

FIG. 6, comprising (FIG. 6A) One hundred μg of Ψ-modified T7TSLucA$_{30}$ RNA was applied to the HPLC column and 3 fractions were collected, all RNAs eluting before the main transcription product (I), the expected RNA (II), and all RNAs eluting after the main transcription product (III). The gradient began at 38% Buffer B and increased to 43% Buffer B over 2.5 min and then spanned 43% to 65% Buffer B over 22 min. Unmodified and m5C/Ψ-modified T7TSLucA$_{30}$ RNA had similar fractions obtained. (FIG. 6B) The RNAs from each fraction were complexed to TransIT and added to DCs and IFN-α in the supernatant was measured 24 hr later. Error bars are standard error of the mean. (FIG. 6C) Two hundred ng of RNA from the 3 fractions and the starting unpurified RNA were blotted and analyzed with the J2 dsRNA-specific mAb.

FIG. 8, comprising FIGS. 8A-8B, depicts the results of analyses showing that RNA contaminants are removed by treatment with RNase III. One hundred μg of U, Ψ, m5C/Ψ, or 1-Me-Ψ-modified TEV-ren-A51 RNA was treated with 0.001 units of bacterial RNase III for 60 minutes at 37° C. in 66 mM acetate buffer, pH=7.5. Similar results were obtained with ranges of RNase III from about 0.001 to about 0.1 units, with treatment times ranging from about 15 to about 120 minutes, and concentrations of acetate buffer ranging from about 33 to about 200 mM and pHs ranging from about 7.5 to about 8.0. After precipitation, washing and resuspension in water, 200 ng of RNA was analyzed for binding by the dsRNA-specific mAb J2 (FIG. 8A) or 300 ng of RNA was complexed to TransIT and added to primary human monocyte derived dendritic cells (FIG. 8B). After 24 hrs, supernatant was analyzed for interferon (IFN)-α.

DETAILED DESCRIPTION OF THE INVENTION

Figure 1A:
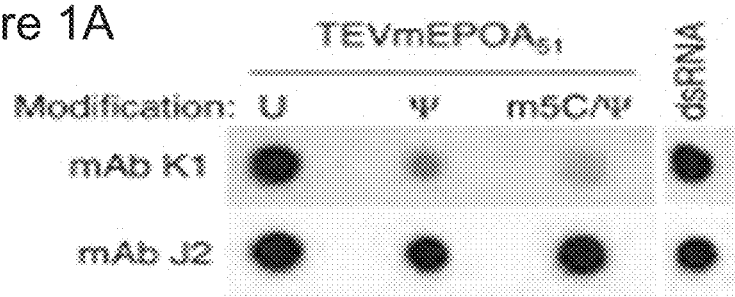
FIGS. 1A-1C, depicts the results of experiments demonstrating that in vitro transcribed RNA is immunogenic and contains dsRNA contaminants.

This invention provides methods of preparing and assessing purified preparations of an RNA, oligoribonucleotide, or polyribonucleotide comprising pseudouridine or a modified nucleoside, purified preparations of gene therapy vectors comprising pseudouridine or a modified nucleoside, as well as methods of reducing immunogenicity and of increasing translation through the use of purified preparations of an RNA, oligoribonucleotide, polyribonucleotide or gene therapy vector comprising pseudouridine or a modified nucleoside.

In one embodiment, the present invention provides a purified preparation of messenger RNA comprising a 1-methyl-pseudouridine residue. In another embodiment, the messenger RNA encodes a protein of interest.

In another embodiment, the present invention provides a purified preparation of an RNA encoding a protein of interest, the RNA comprising at least one 1-methyl-pseudouridine residue.

In another embodiment, the present invention provides a purified preparation of an in vitro-transcribed RNA molecule, comprising a 1-methyl-pseudouridine.

In another embodiment, the present invention provides a purified preparation of an in vitro-transcribed RNA molecule, comprising a modified nucleoside.

As provided herein, the present invention provides methods for purifying and assessing purity of in vitro-transcribed RNA molecules, comprising 1-methyl-pseudouridine and/or modified nucleosides.

In another embodiment, the present invention provides a purified preparation of a messenger RNA comprising at least one 1-methyl-pseudouridine residue.

In another embodiment, the purified preparation of in vitro-transcribed RNA is synthesized by T7 phage RNA polymerase. In another embodiment, the purified preparation of in vitro-transcribed RNA is synthesized by SP6 phage RNA polymerase. In another embodiment, the purified preparation of in vitro-transcribed RNA is synthesized by T3 phage RNA polymerase. In another embodiment, the purified preparation of in vitro-transcribed RNA is synthesized by any known in vitro chemical synthesis method, such as those known in the art.

In another embodiment, the purified preparation of in vitro-transcribed RNA is an oligoribonucleotide. In another embodiment, the purified preparation of the in vitro-transcribed RNA is a polyribonucleotide.

In another embodiment, the present invention provides a purified preparation of an in vitro-synthesized oligoribonucleotide, comprising a 1-methyl-pseudouridine or a modified nucleoside, wherein the modified nucleoside is pseudouridine (Ψ), m5C, m5U, m6A, s2U, 2'-O-methyl-C, 2'-O-methyl-A, 2'-O-methyl-G, or 2'-O-methyl-U.

In another embodiment, the present invention provides a purified preparation of an in vitro-synthesized polyribonucleotide, comprising a 1-methyl-pseudouridine or a modified nucleoside, wherein the modified nucleoside is pseudouridine (Ψ), m5C, m5U, m6A, s2U, 2'-O-methyl-C, 2'-O-methyl-A, 2'-O-methyl-G, or 2'-O-methyl-U.

In another embodiment, the purified preparation of in vitro-synthesized oligoribonucleotide or polyribonucleotide is a short hairpin (sh)RNA. In a particular non-limiting embodiment, the purified preparation of in vitro-synthesized oligoribonucleotide or polyribonucleotide is a cas9 guide RNA. In another embodiment, the purified preparation of in vitro-synthesized oligoribonucleotide is a small interfering RNA (siRNA). In another embodiment, the purified preparation of in vitro-synthesized oligoribonucleotide is any other type of oligoribonucleotide known in the art.

In another embodiment, the purified preparation of an RNA, oligoribonucleotide, or polyribonucleotide of the methods and compositions of the present invention further comprise an open reading frame that encodes a functional protein. In another embodiment, the purified preparation of an RNA or a oligoribonucleotide functions without encoding a functional protein (e.g., in transcriptional silencing), such as an RNAzyme, etc.

In another embodiment, the purified preparation of RNA, oligoribonucleotide, or polyribonucleotide further comprises a poly-A tail. In another embodiment, the purified preparation of the RNA, oligoribonucleotide, or polyribonucleotide does not comprise a poly-A tail.

In another embodiment, the purified preparation of RNA, oligoribonucleotide, or polyribonucleotide further comprises an m7GpppG cap. In another embodiment, the purified preparation of the RNA, oligoribonucleotide, or polyribonucleotide does not comprise an m7GpppG cap.

In another embodiment, the purified preparation of the RNA, oligoribonucleotide, or polyribonucleotide further comprises a cap-independent translational enhancer. In another embodiment, the purified preparation of the RNA, oligoribonucleotide, or polyribonucleotide does not comprise a cap-independent translational enhancer. In one embodiment, the cap-independent translational enhancer is a tobacco etch virus (TEV) cap-independent translational enhancer.

In another embodiment, the present invention provides a purified preparation of a gene-therapy vector, comprising an in vitro-synthesized polyribonucleotide, wherein the polyribonucleotide comprises a 1-methyl-pseudouridine or a modified nucleoside.

In another embodiment, the purified preparation of an RNA, oligoribonucleotide, or polyribonucleotide of the methods and compositions of the present invention comprises a 1-methyl-pseudouridine. In another embodiment, the purified preparation of the RNA or oligoribonucleotide comprises a modified nucleoside. In another embodiment, the purified preparation of the RNA or oligoribonucleotide is an in vitro-synthesized RNA or oligoribonucleotide.

In one embodiment, the modified nucleoside is Ψ (pseudouridine). In one embodiment, the modified nucleoside is m1acp3Ψ (1-methyl-3-(3-amino-3-carboxypropyl) pseudouridine. In another embodiment, the modified nucleoside is m1Ψ (1-methylpseudouridine). In another embodiment, the modified nucleoside is Ψm (2'-O-methylpseudouridine). In another embodiment, the modified nucleoside is m5D (5-methyldihydrouridine). In another embodiment, the modified nucleoside is m3Ψ (3-methylpseudouridine). In another embodiment, the modified nucleoside is a pseudouridine moiety that is not further modified. In another embodiment, the modified nucleoside is any other pseudouridine known in the art.

In another embodiment, the purified preparation of an RNA, oligoribonucleotide, or polyribonucleotide of methods and compositions of the present invention is a therapeutic oligoribonucleotide.

In another embodiment, the present invention provides a method for delivering a recombinant protein to a subject, the method comprising the step of contacting the subject with a purified preparation of an RNA, oligoribonucleotide, polyribonucleotide molecule, or a purified preparation of a gene-therapy vector of the present invention, thereby delivering a recombinant protein to a subject.

In another embodiment, the length of an RNA, oligoribonucleotide, or polyribonucleotide (e.g., a single-stranded RNA (ssRNA) or dsRNA molecule) of methods and compositions of the present invention is greater than 30 nucleotides in length. In another embodiment, the RNA or oligoribonucleotide is greater than 35 nucleotides in length. In another embodiment, the length is at least 40 nucleotides. In another embodiment, the length is at least 45 nucleotides. In another embodiment, the length is at least 55 nucleotides. In another embodiment, the length is at least 60 nucleotides. In another embodiment, the length is at least 60 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1800 nucleotides. In another embodiment, the length is at least 2000 nucleotides. In another embodiment, the length is at least 2500 nucleotides. In another embodiment, the length is at least 3000 nucleotides. In another embodiment, the length is at least 4000 nucleotides. In another embodiment, the length is at least 5000 nucleotides. In another embodiment, the length is at least 10000 nucleotides. In another embodiment, the length is at least 20000 nucleotides.

In another embodiment, the purified preparation of mRNA of methods and compositions of the present invention is manufactured by in vitro transcription.

In another embodiment, the step of in vitro transcription utilizes T7 phage RNA polymerase. In another embodiment, the in vitro transcription utilizes SP6 phage RNA polymerase. In another embodiment, the in vitro transcription utilizes T3 phage RNA polymerase. In another embodiment, the in vitro transcription utilizes an RNA polymerase selected from the above polymerases. In another embodiment, the in vitro transcription utilizes any other RNA polymerase, or modified DNA polymerase, known in the art. In another embodiment, the in vitro transcription utilizes chemical synthesis.

In another embodiment, the nucleoside that is modified in an RNA, oligoribonucleotide, or polyribonucleotide of the methods and compositions of the present invention is uridine (U). In another embodiment, the modified nucleoside is cytidine (C). In another embodiment, the modified nucleoside is adenine (A). In another embodiment the modified nucleoside is guanine (G).

In another embodiment, the modified nucleoside of the methods and compositions of the present invention is m5C (5-methylcytidine). In another embodiment, the modified nucleoside is m5U (5-methyluridine). In another embodiment, the modified nucleoside is m6A (N6-methyladenosine). In another embodiment, the modified nucleoside is s2U (2-thiouridine). In another embodiment, the modified nucleoside is Ψ (pseudouridine). In another embodiment, the modified nucleoside is Um (2'-O-methyluridine).

In other embodiments, the modified nucleoside is m1A (1-methyladenosine); m2A (2-methyladenosine); Am (2'-O-methyladenosine); ms2m6A (2-methylthio-N6-methyladenosine); i6A (N6-isopentenyladenosine); ms2i6A (2-methylthio-N6isopentenyladenosine); io6A (N6-(cis-hydroxyisopentenyl)adenosine); ms2io6A (2-methylthio-N6-(cis-hydroxyisopentenyl) adenosine); g6A (N6-glycinylcarbamoyladenosine); t6A (N6-threonylcarbamoyladenosine); ms2t6A (2-methylthio-N6-threonyl carbamoyladenosine); m6t6A (N6-methyl-N6-threonylcarbamoyladenosine); hn6A(N6-hydroxynorvalylcarbamoyladenosine); ms2hn6A (2-methylthio-N6-hydroxynorvalyl carbamoyladenosine); Ar(p) (2'-O-ribosyladenosine (phosphate)); I (inosine); m1I (1-methylinosine); m1Im (1,2'-O-dimethylinosine); m3C (3-methylcytidine); Cm (2'-O-methylcytidine); s2C (2-thiocytidine); ac4C (N4-acetylcytidine); f5C (5-formylcytidine); m5Cm (5,2'-O-dimethylcytidine); ac4Cm (N4-acetyl-2'-O-methylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); preQ0 (7-cyano-7-deazaguanosine); preQ1 (7-aminomethyl-7-deazaguanosine); G+ (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonylmethyluridine); mcm5Um (5-methoxycarbonylmethyl-2'-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyluridine); ncm5Um (5-carbamoylmethyl-2'-O-methyluridine); cmnm5U (5-carboxymethylaminomethyluridine); cmnm5Um (5-carboxymethylaminomethyl-2'-O-methyluridine); cmnm5s2U (5-carboxymethylaminomethyl-2-thiouridine); m62A (N6,N6-dimethyladenosine); Im (2'-O-methylinosine); m4C (N4-methylcytidine); m4Cm (N4,2'-O-dimethylcytidine); hm5C (5-hydroxymethylcytidine); m3U (3-methyluridine); cm5U (5-carboxymethyluridine); m6Am (N6,2'-O-dimethyladenosine); m62Am (N6,N6,O-2'-trimethyladenosine); m2,7G (N2,7-dimethylguanosine); m2,2,7G (N2,N2,7-trimethylguanosine); m3Um (3,2'-O-dimethyluridine); m5D (5-methyldihydrouridine); f5Cm (5-formyl-2'-O-methylcytidine); m1Gm (1,2'-O-dimethylguanosine); m1Am (1,2'-O-dimethyladenosine); τm5U (5-taurinomethyluridine); τM5s2U (5-taurinomethyl-2-thiouridine)); imG-14 (4-demethylwyosine); imG2 (isowyosine); or ac6A (N6-acetyladenosine).

In another embodiment, the purified preparation of RNA, oligoribonucleotide, or polyribonucleotide of the methods and compositions of the present invention comprises a combination of two or more of the above-described modifications. In another embodiment, the purified preparation of the RNA or oligoribonucleotide comprises a combination of three or more of the above-described modifications. In another embodiment, the purified preparation of the RNA or oligoribonucleotide comprises a combination of more than three of the above-described modifications.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

In another embodiment, between 0.1% and 100% of the residues in the RNA, oligoribonucleotide, or polyribonucleotide of the methods and compositions of the present invention are modified (e.g., either by the presence of pseudouridine or a modified nucleoside base). In another embodiment, 0.1% of the residues are modified. In another embodiment, 0.2% of the residues are modified. In another embodiment, 0.3% of the residues are modified. In another embodiment, 0.4% of the residues are modified. In another embodiment, 0.5% of the residues are modified. In another embodiment, 0.6% of the residues are modified. In another embodiment, 0.8% of the residues are modified. In another embodiment, 1% of the residues are modified. In another embodiment, 1.5% of the residues are modified. In another embodiment, 2% of the residues are modified. In another embodiment, 2.5% of the residues are modified. In another embodiment, 3% of the residues are modified. In another embodiment, 4% of the residues are modified. In another embodiment, 5% of the residues are modified. In another embodiment, 6% of the residues are modified. In another embodiment, 8% of the residues are modified. In another embodiment, 10% of the residues are modified. In another embodiment, 12% of the residues are modified. In another embodiment, 14% of the residues are modified. In another embodiment, 16% of the residues are modified. In another embodiment, 18% of the residues are modified. In another embodiment, 20% of the residues are modified. In another embodiment, 25% of the residues are modified. In another embodiment, 30% of the residues are modified. In another embodiment, 35% of the residues are modified. In another embodiment, 40% of the residues are modified. In another embodiment, 45% of the residues are modified. In another embodiment, 50% of the residues are modified. In another embodiment, 60% of the residues are modified. In another embodiment, 70% of the residues are modified. In another embodiment, 80% of the residues are modified. In another embodiment, 90% of the residues are modified. In another embodiment, 100% of the residues are modified.

In another embodiment, less than 5% of the residues are modified. In another embodiment, less than 3% of the residues are modified. In another embodiment, less than 1% of the residues are modified. In another embodiment, less than 2% of the residues are modified. In another embodiment, the fraction is less than 4% of the residues are modified. In another embodiment, less than 6% of the residues are modified. In another embodiment, less than 8% of the residues are modified. In another embodiment, less than 10% of the residues are modified. In another embodiment, less than 12% of the residues are modified. In another embodiment, less than 15% of the residues are modified. In another embodiment, less than 20% of the residues are modified. In another embodiment, less than 30% of the residues are modified. In another embodiment, less than 40% of the residues are modified. In another embodiment, less than 50% of the residues are modified. In another embodiment, less than 60% of the residues are modified. In another embodiment, less than 70% of the residues are modified.

In another embodiment, 0.1% of the residues of a given nucleotide (uridine, cytidine, guanosine, or adenine) are modified. In another embodiment, the fraction of the given nucleotide that is modified is 0.2%. In another embodiment, the fraction of the given nucleotide that is modified is 0.3%. In another embodiment, the fraction of the given nucleotide that is modified is 0.4%. In another embodiment, the fraction of the given nucleotide that is modified is 0.5%. In another embodiment, the fraction of the given nucleotide that is modified is 0.6%. In another embodiment, the fraction of the given nucleotide that is modified is 0.8%. In another embodiment, the fraction of the given nucleotide that is modified is 1%. In another embodiment, the fraction of the given nucleotide that is modified is 1.5%. In another embodiment, the fraction of the given nucleotide that is modified is 2%. In another embodiment, the fraction of the given nucleotide that is modified is 2.5%. In another embodiment, the fraction of the given nucleotide that is modified is 3%. In another embodiment, the fraction of the given nucleotide that is modified is 4%. In another embodiment, the fraction of the given nucleotide that is modified is 5%. In another embodiment, the fraction of the given nucleotide that is modified is 6%. In another embodiment, the fraction of the given nucleotide that is modified is 8%. In another embodiment, the fraction of the given nucleotide that is modified is 10%. In another embodiment, the fraction of the given nucleotide that is modified is 12%. In another embodiment, the fraction of the given nucleotide that is modified is 14%. In another embodiment, the fraction of the given nucleotide that is modified is 16%. In another embodiment, the fraction of the given nucleotide that is modified is 18%. In another embodiment, the fraction of the given nucleotide that is modified is 20%. In another embodiment, the fraction of the given nucleotide that is modified is 25%. In another embodiment, the fraction of the given nucleotide that is modified is 30%. In another embodiment, the fraction of the given nucleotide that is modified is 35%. In another embodiment, the fraction of the given nucleotide that is modified is 40%. In another embodiment, the fraction of the given nucleotide that is modified is 45%. In another embodiment, the fraction of the given nucleotide that is modified is 50%. In another embodiment, the fraction of the given nucleotide that is modified is 60%. In another embodiment, the fraction of the given nucleotide that is modified is 70%. In another embodiment, the fraction of the given nucleotide that is modified is 80%. In another embodiment, the fraction of the given nucleotide that is modified is 90%. In another embodiment, the fraction of the given nucleotide that is modified is 100%.

In another embodiment, the fraction of the given nucleotide that is modified is less than 8%. In another embodiment, the fraction of the given nucleotide that is modified is less than 10%. In another embodiment, the fraction of the given nucleotide that is modified is less than 5%. In another embodiment, the fraction of the given nucleotide that is modified is less than 3%. In another embodiment, the fraction of the given nucleotide that is modified is less than 1%. In another embodiment, the fraction of the given nucleotide that is modified is less than 2%. In another embodiment, the fraction of the given nucleotide that is modified is less than 4%. In another embodiment, the fraction of the given nucleotide that is modified is less than 6%. In another embodiment, the fraction of the given nucleotide that is modified is less than 12%. In another embodiment, the fraction of the given nucleotide that is modified is less than 15%. In another embodiment, the fraction of the given nucleotide that is modified is less than 20%. In another embodiment, the fraction of the given nucleotide that is modified is less than 30%. In another embodiment, the fraction of the given nucleotide that is modified is less than 40%. In another embodiment, the fraction of the given nucleotide that is modified is less than 50%. In another embodiment, the fraction of the given nucleotide that is modified is less than 60%. In another embodiment, the fraction is less than 70%.

In another embodiment, the terms "ribonucleotide," "oligoribonucleotide," and "polyribonucleotide" refers to a string of at least 2 base-sugar-phosphate combinations. The term includes, in another embodiment, compounds comprising nucleotides in which the sugar moiety is ribose. In another embodiment, the term includes both RNA and RNA derivatives in which the backbone is modified. "Nucleotides" refers to the monomeric units of nucleic acid polymers. RNA may be, in another embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy et al., Genes & Devel 16: 2491-96 and references cited therein). In addition, these forms of RNA may be single, double, triple, or quadruple stranded. The term also includes, in another embodiment, artificial nucleic acids that may contain other types of backbones but the same bases. In another embodiment, the artificial nucleic acid is a PNA (peptide nucleic acid). PNA contain peptide backbones and nucleotide bases and are able to bind, in another embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen, Curr Opin Struct Biol 9:353-57; and Raz et al., Biochem Biophys Res Commun. 297:1075-84. The production and use of nucleic acids is known to those skilled in art and is described, for example, in Molecular Cloning, (2012), Sambrook and Russell, eds. and Methods in Enzymology: Methods for molecular cloning in eukaryotic cells (2003) Purchio and G. C. Fareed. Each nucleic acid derivative represents a separate embodiment of the present invention In another embodiment, the term "oligoribonucleotide" refers to a string comprising fewer than 25 nucleotides (nt). In another embodiment, "oligoribonucleotide" refers to a string of fewer than 24 nucleotides. In another embodiment, "oligoribonucleotide" refers to a string of fewer than 23 nucleotides. In another embodiment, "oligoribonucleotide" refers to a string of fewer than 22 nucleotides. In another embodiment, "oligoribonucleotide" refers to a string of fewer than 21 nucleotides. In another embodiment, "oligoribonucleotide" refers to a string of fewer than 20 nucleotides. In another embodiment, "oligoribonucleotide" refers to a string of fewer than 19 nucleotides. In another embodiment, "oligoribonucleotide" refers to a string of fewer than 18 nucleotides. In another embodiment, "oligoribonucleotide" refers to a string of fewer than 17 nucleotides. In another embodiment, "oligoribonucleotide" refers to a string of fewer than 16 nucleotides.

In another embodiment, the term "polyribonucleotide" refers to a string comprising more than 25 nucleotides (nt). In another embodiment, "polyribonucleotide" refers to a string of more than 26 nucleotides. In another embodiment, "polyribonucleotide" refers to a string of more than 28 nucleotides. In another embodiment, "polyribonucleotide" refers to a string of more than 30 nucleotides. In another embodiment, "polyribonucleotide" refers to a string of more than 32 nucleotides. In another embodiment, "polyribonucleotide" refers to a string of more than 35 nucleotides. In another embodiment, "polyribonucleotide" refers to a string of more than 40 nucleotides. In another embodiment, "polyribonucleotide" refers to a string of more than 50 nucleotides. In another embodiment, "polyribonucleotide" refers to a string of more than 60 nucleotides. In another embodiment, "polyribonucleotide" refers to a string of more than 80 nucleotides. In another embodiment, "polyribonucleotide" refers to a string of more than 100 nucleotides. In another embodiment, "polyribonucleotide" refers to a string of more than 120 nucleotides. In another embodiment, "polyribonucleotide" refers to a string of more than 150 nucleotides. In another embodiment, "polyribonucleotide" refers to a string of more than 200 nucleotides. In another embodiment, "polyribonucleotide" refers to a string of more than 300 nucleotides. In another embodiment, "polyribonucleotide" refers to a string of more than 400 nucleotides. In another embodiment, "polyribonucleotide" refers to a string of more than 500 nucleotides. In another embodiment, "polyribonucleotide" refers to a string of more than 600 nucleotides. In another embodiment, "polyribonucleotide" refers to a string of more than 800 nucleotides. In another embodiment, "polyribonucleotide" refers to a string of more than 1000 nucleotides. In another embodiment, "polyribonucleotide" refers to a string of more than 1200 nucleotides. In another embodiment, "polyribonucleotide" refers to a string of more than 1400 nucleotides. In another embodiment, "polyribonucleotide" refers to a string of more than 1600 nucleotides. In another embodiment, "polyribonucleotide" refers to a string of more than 1800 nucleotides. In another embodiment, "polyribonucleotide" refers to a string of more than 2000 nucleotides.

As used herein, "purified preparation" means that the nucleic acid preparation predominately contains the nucleic acid of interest and is substantially free of other nucleic acids which are not the nucleic acid of interest. In one embodiment, at least about 75% the nucleic acid present in the purified preparation of the invention is the nucleic acid of interest. In another embodiment, at least about 76% the nucleic acid present in the purified preparation of the invention is the nucleic acid of interest. In another embodiment, at least about 77% the nucleic acid present in the purified preparation of the invention is the nucleic acid of interest. In another embodiment, at least about 78% the nucleic acid present in the purified preparation of the invention is the nucleic acid of interest. In another embodiment, at least about 79% the nucleic acid present in the purified preparation of the invention is the nucleic acid of interest. In another embodiment, at least about 80% the nucleic acid present in the purified preparation of the invention is the nucleic acid of interest. In another embodiment, at least about 81% the nucleic acid present in the purified preparation of the invention is the nucleic acid of interest. In another embodiment, at least about 82% the nucleic acid present in the purified preparation of the invention is the nucleic acid of interest.

In another embodiment, at least about 83% the nucleic acid present in the purified preparation of the invention is the nucleic acid of interest. In another embodiment, at least about 84% the nucleic acid present in the purified preparation of the invention is the nucleic acid of interest. In another embodiment, at least about 85% the nucleic acid present in the purified preparation of the invention is the nucleic acid of interest. In another embodiment, at least about 86% the nucleic acid present in the purified preparation of the invention is the nucleic acid of interest. In another embodiment, at least about 87% the nucleic acid present in the purified preparation of the invention is the nucleic acid of interest. In another embodiment, at least about 88% the nucleic acid present in the purified preparation of the invention is the nucleic acid of interest. In another embodiment, at least about 89% the nucleic acid present in the purified preparation of the invention is the nucleic acid of interest. In another embodiment, at least about 90% the nucleic acid present in the purified preparation of the invention is the nucleic acid of interest. In another embodiment, at least about 91% the nucleic acid present in the purified preparation of the invention is the nucleic acid of interest. In another embodiment, at least about 92% the nucleic acid present in the purified preparation of the invention is the nucleic acid of interest. In another embodiment, at least about 93% the nucleic acid present in the purified preparation of the invention is the nucleic acid of interest. In another embodiment, at least about 94% the nucleic acid present in the purified preparation of the invention is the nucleic acid of interest. In another embodiment, at least about 95% the nucleic acid present in the purified preparation of the invention is the nucleic acid of interest. In another embodiment, at least about 96% the nucleic acid present in the purified preparation of the invention is the nucleic acid of interest. In another embodiment, at least about 97% the nucleic acid present in the purified preparation of the invention is the nucleic acid of interest. In another embodiment, at least about 98.1% the nucleic acid present in the purified preparation of the invention is the nucleic acid of interest. In another embodiment, at least about 98.2% the nucleic acid present in the purified preparation of the invention is the nucleic acid of interest. In another embodiment, at least about 98.3% the nucleic acid present in the purified preparation of the invention is the nucleic acid of interest. In another embodiment, at least about 98.4% the nucleic acid present in the purified preparation of the invention is the nucleic acid of interest. In another embodiment, at least about 98.5% the nucleic acid present in the purified preparation of the invention is the nucleic acid of interest. In another embodiment, at least about 98.6% the nucleic acid present in the purified preparation of the invention is the nucleic acid of interest. In another embodiment, at least about 98.7% the nucleic acid present in the purified preparation of the invention is the nucleic acid of interest. In another embodiment, at least about 98.8% the nucleic acid present in the purified preparation of the invention is the nucleic acid of interest. In another embodiment, at least about 98.9% the nucleic acid present in the purified preparation of the invention is the nucleic acid of interest. In another embodiment, at least about 99.0% the nucleic acid present in the purified preparation of the invention is the nucleic acid of interest. In another embodiment, at least about 99.1% the nucleic acid present in the purified preparation of the invention is the nucleic acid of interest. In another embodiment, at least about 99.2% the nucleic acid present in the purified preparation of the invention is the nucleic acid of interest. In another embodiment, at least about 99.3% the nucleic acid present in the purified preparation of the invention is the nucleic acid of interest. In another embodiment, at least about 99.4% the nucleic acid present in the purified preparation of the invention is the nucleic acid of interest. In another embodiment, at least about 99.5% the nucleic acid present in the purified preparation of the invention is the nucleic acid of interest. In another embodiment, at least about 99.6% the nucleic acid present in the purified preparation of the invention is the nucleic acid of interest. In another embodiment, at least about 99.7% the nucleic acid present in the purified preparation of the invention is the nucleic acid of interest. In another embodiment, at least about 99.8% the nucleic acid present in the purified preparation of the invention is the nucleic acid of interest. In another embodiment, at least about 99.9% the nucleic acid present in the purified preparation of the invention is the nucleic acid of interest.

The nucleic acid of interest can be purified by any method known in the art, or any method to be developed, so long as the method of purification removes contaminants from the nucleic acid preparation and thereby substantially reduces the immunogenicity potential of the nucleic acid preparation. In one embodiment, the nucleic acid of interest is purified using high-performance liquid chromatography (HPLC). In another embodiment, the nucleic acid of interest is purified by contacting the nucleic acid of interest with the bacterial enzyme RNase III. In other various embodiments, any method of nucleic acid purification that substantially reduces the immunogenicity of the nucleic acid preparation can be used. Non-limiting examples of purification methods that can be used with the compositions and methods of the invention liquid chromatography separation and enzyme digestion, each used alone or in any combination, simultaneously or in any order. Non-limiting examples of liquid chromatography separation include HPLC and fast protein liquid chromatography (FPLC). Materials useful in the HPLC and FPLC methods of the invention include, but are not limited to, cross-linked polystyrene/divinylbenzene (PS/DVB), PS/DVB-C18, PS/DVB-alkylated, Helix DNA columns (Varian), Eclipse dsDNA Analysis Columns (Agilent Technologies), Reverse-phase 5 (RPC-5) exchange material, DNAPac, ProSwift, and bio-inert UltiMate® 3000 Titanium columns (Dionex). Enzymes useful in the enzyme digestion methods of the invention include any enzyme able to digest any contaminant in a nucleic acid preparation of the invention, such as, for example a dsRNA contaminant, and include but are not limited to, RNase III, RNase V1, Dicer, and Chipper (see Fruscoloni et al., 2002, PNAS 100:1639) Non-limiting examples of assays for assessing the purity of the nucleic acid of interest include a dot-blot assay, a Northern blot assay, and a dendritic cell activation assay, as described elsewhere herein.

In another embodiment, the present invention provides a method for inducing a mammalian cell to produce a protein of interest, comprising contacting the mammalian cell with a purified preparation of an in vitro-synthesized RNA comprising a 1-methyl-pseudouridine or a modified nucleoside and encoding a recombinant protein, thereby inducing a mammalian cell to produce a protein of interest. In another embodiment, the protein of interest is a recombinant protein.

"Encoding" refers, in another embodiment, to an RNA that contains a gene that encodes the protein of interest. In another embodiment, the RNA comprises an open reading frame that encodes the protein of interest. In another embodiment, one or more other proteins are also encoded. In another embodiment, the protein of interest is the only protein encoded.

In another embodiment, the present invention provides a method of inducing a mammalian cell to produce a recombinant protein, comprising contacting the mammalian cell with a purified preparation of an in vitro-transcribed RNA comprising a pseudouridine or a modified nucleoside and encoding a recombinant protein, thereby inducing a mammalian cell to produce a recombinant protein.

In another embodiment, the purified preparation of an RNA, oligoribonucleotide, or polyribonucleotide of methods and compositions of the present invention is translated in the cell more efficiently than an unmodified RNA and/or unpurified RNA with the same sequence. In another embodiment, the purified preparation of the RNA, oligoribonucleotide, or polyribonucleotide exhibits enhanced ability to be translated by a target cell. In another embodiment, translation is enhanced by a factor of 2-fold relative to its unmodified and/or unpurified counterpart. In another embodiment, translation is enhanced by a 3-fold factor. In another embodiment, translation is enhanced by a 5-fold factor. In another embodiment, translation is enhanced by a 7-fold factor. In another embodiment, translation is enhanced by a 10-fold factor. In another embodiment, translation is enhanced by a 15-fold factor. In another embodiment, translation is enhanced by a 20-fold factor. In another embodiment, translation is enhanced by a 50-fold factor. In another embodiment, translation is enhanced by a 100-fold factor. In another embodiment, translation is enhanced by a 200-fold factor. In another embodiment, translation is enhanced by a 500-fold factor. In another embodiment, translation is enhanced by a 1000-fold factor. In another embodiment, translation is enhanced by a 2000-fold factor. In another embodiment, the factor is 10-1000-fold. In another embodiment, the factor is 10-100-fold. In another embodiment, the factor is 10-200-fold. In another embodiment, the factor is 10-300-fold. In another embodiment, the factor is 10-500-fold. In another embodiment, the factor is 20-1000-fold. In another embodiment, the factor is 30-1000-fold. In another embodiment, the factor is 50-1000-fold. In another embodiment, the factor is 100-1000-fold. In another embodiment, the factor is 200-1000-fold. In another embodiment, translation is enhanced by any other significant amount or range of amounts.

Methods of determining translation efficiency are well known in the art, and include, e.g., measuring the activity of an encoded reporter protein (e.g., luciferase or *Renilla* or green fluorescent protein (Wall et al., J Biol Chem 2005; 280(30): 27670-8), or measuring radioactive label incorporated into the translated protein (Ngosuwan et al., 2003, J Biol Chem 278:7034-42).

In some embodiments, translation is measured from RNA complexed to Lipofectin® (Gibco BRL, Gaithersburg, MD, USA) and injected into the tail vein of mice. In the spleen lysates, 1-methyl-pseudouridine-modified RNA was translated significantly more efficiently than unmodified RNA (see U.S. Pat. No. 8,278,036). Under the conditions utilized, efficiency of transfection-based methods of the present invention correlates with the ability of the transfection reagent to penetrate into tissues.

In another embodiment, the enhanced translation is in a cell (relative to translation in the same cell of an unmodified RNA, or a modified but unpurified RNA, with the same sequence. In another embodiment, the enhanced translation is in vitro (e.g. in an in vitro translation mix or a reticulocyte lysate). In another embodiment, the enhanced translation is in vivo. In each case, the enhanced translation is relative to an unmodified RNA, or a modified but unpurified RNA, with the same sequence, under the same conditions.

In another embodiment, the purified preparation of the RNA, oligoribonucleotide, or polyribonucleotide of methods and compositions of the present invention is significantly less immunogenic than an unmodified in vitro-synthesized RNA with the same sequence, or compared with the unpurified, modified in vitro-synthesized RNA with the same sequence. In another embodiment, the purified RNA is 2-fold less immunogenic than its unpurified counterpart. In another embodiment, immunogenicity is reduced by a 3-fold factor. In another embodiment, immunogenicity is reduced by a 5-fold factor. In another embodiment, immunogenicity is reduced by a 7-fold factor. In another embodiment, immunogenicity is reduced by a 10-fold factor. In another embodiment, immunogenicity is reduced by a 15-fold factor. In another embodiment, immunogenicity is reduced by a 20-fold factor. In another embodiment, immunogenicity is reduced by a 50-fold factor. In another embodiment, immunogenicity is reduced by a 100-fold factor. In another embodiment, immunogenicity is reduced by a 200-fold factor. In another embodiment, immunogenicity is reduced by a 500-fold factor. In another embodiment, immunogenicity is reduced by a 1000-fold factor. In another embodiment, immunogenicity is reduced by a 2000-fold factor. In another embodiment, immunogenicity is reduced by another fold difference.

In another embodiment, "significantly less immunogenic" refers to a detectable decrease in immunogenicity. In another embodiment, the term refers to a fold decrease in immunogenicity (e.g., 1 of the fold decreases enumerated above). In another embodiment, the term refers to a decrease such that an effective amount of the purified preparation of RNA, oligoribonucleotide, or polyribonucleotide can be administered without triggering a detectable immune response. In another embodiment, the term refers to a decrease such that the purified preparation of RNA, oligoribonucleotide, or polyribonucleotide can be repeatedly administered without eliciting an immune response sufficient to detectably reduce expression of the recombinant protein. In another embodiment, the decrease is such that the purified preparation of RNA, oligoribonucleotide, or polyribonucleotide can be repeatedly administered without eliciting an immune response sufficient to eliminate detectable expression of the recombinant protein.

"Effective amount" of the purified preparation of RNA, oligoribonucleotide, or polyribonucleotide refers, in another embodiment, to an amount sufficient to exert a therapeutic effect. In another embodiment, the term refers to an amount sufficient to elicit expression of a detectable amount of the recombinant protein.

Methods of determining immunogenicity are well known in the art, and include, e.g. measuring secretion of cytokines (e.g. IL-12, IFN-α, TNF-α, RANTES, MIP-1α or β, IL-6, IFN-β, or IL-8), measuring expression of DC activation markers (e.g. CD83, HLA-DR, CD80 and CD86), or measuring ability to act as an adjuvant for an adaptive immune response.

In another embodiment, the relative immunogenicity of the modified nucleotide and its unmodified counterpart, as well as the purified nucleotide and its unpurified counterpart, are determined by determining the quantity of the nucleotide required to elicit one of the above responses to the same degree as a given quantity of the unmodified or unpurified nucleotide. For example, if twice as much nucleotide (e.g., modified and/or purified) is required to elicit the same response, than the nucleotide is two-fold less immunogenic than the unmodified or unpurified nucleotide.

In another embodiment, the relative immunogenicity of the purified nucleotide and its unpurified counterpart are determined by determining the quantity of cytokine (e.g. IL-12, IFN-α, TNF-α, RANTES, MIP-1α or β, IL-6, IFN-β, or IL-8) secreted in response to administration of the purified nucleotide, relative to the same quantity of the unpurified nucleotide. For example, if one-half as much cytokine is secreted, than the purified nucleotide is two-fold less immunogenic than the unpurified nucleotide. In another embodiment, background levels of stimulation are subtracted before calculating the immunogenicity in the above methods.

In another embodiment, a method of present invention further comprises mixing the purified preparation of RNA, oligoribonucleotide, or polyribonucleotide with a transfection reagent prior to the step of contacting a target cell. In another embodiment, a method of present invention further comprises administering the purified preparation of RNA, oligoribonucleotide, or polyribonucleotide together with the transfection reagent. In another embodiment, the transfection reagent is a cationic lipid reagent.

In another embodiment, the transfection reagent is a lipid-based transfection reagent. In another embodiment, the transfection reagent is a protein-based transfection reagent. In another embodiment, the transfection reagent is a carbohydrate-based transfection reagent. In another embodiment, the transfection reagent is a polyethyleneimine-based transfection reagent. In another embodiment, the transfection reagent is calcium phosphate. In another embodiment, the transfection reagent is Lipofectin® or Lipofectamine®. In another embodiment, the transfection reagent is a lipid nanoparticle (Semple et al., 2010, Nat Biotechnol. 28(2): 172-176). In another embodiment, the transfection reagent is any other transfection reagent known in the art.

In another embodiment, the transfection reagent forms a liposome. Liposomes, in another embodiment, increase intracellular stability, increase uptake efficiency and improve biological activity. In another embodiment, liposomes are hollow spherical vesicles composed of lipids arranged in a similar fashion as those lipids, which make up the cell membrane. They have, in another embodiment, an internal aqueous space for entrapping water-soluble compounds and range in size from 0.05 to several microns in diameter. In another embodiment, liposomes can deliver RNA to cells in a biologically active form.

In another embodiment, the target cell of methods of the present invention is an antigen-presenting cell. In another embodiment, the cell is an animal cell. In another embodiment, the cell is a dendritic cell. In another embodiment, the cell is a neural cell. In another embodiment, the cell is a brain cell. In another embodiment, the cell is a spleen cell. In another embodiment, the cell is a lymphoid cell. In another embodiment, the cell is a lung cell. In another embodiment, the cell is a skin cell. In another embodiment, the cell is a keratinocyte. In another embodiment, the cell is an endothelial cell. In another embodiment, the cell is an astrocyte, a microglial cell, or a neuron. In another embodiment, the cell is an alveolar cell. In another embodiment, the cell is a surface alveolar cell. In another embodiment, the cell is an alveolar macrophage. In another embodiment, the cell is an alveolar pneumocyte. In another embodiment, the cell is a vascular endothelial cell. In another embodiment, the cell is a mesenchymal cell. In another embodiment, the cell is an epithelial cell. In another embodiment, the cell is a hematopoietic cell. In another embodiment, the cell is colonic epithelium cell. In another embodiment, the cell is a lung epithelium cell. In another embodiment, the cell is a bone marrow cell.

In other embodiments, the target cell is a Claudius' cell, Hensen cell, Merkel cell, Müller cell, Paneth cell, Purkinje cell, Schwann cell, Sertoli cell, acidophil cell, acinar cell, adipoblast, adipocyte, brown or white alpha cell, amacrine cell, beta cell, capsular cell, cementocyte, chief cell, chondroblast, chondrocyte, chromaffin cell, chromophobic cell, corticotroph, delta cell, Langerhans cell, follicular dendritic cell, enterochromaffin cell, ependymocyte, epithelial cell, basal cell, squamous cell, endothelial cell, transitional cell, erythroblast, erythrocyte, fibroblast, fibrocyte, follicular cell, germ cell, gamete, ovum, spermatozoon, oocyte, primary oocyte, secondary oocyte, spermatid, spermatocyte, primary spermatocyte, secondary spermatocyte, germinal epithelium, giant cell, glial cell, astroblast, astrocyte, oligodendroblast, oligodendrocyte, glioblast, goblet cell, gonadotroph, granulosa cell, haemocytoblast, hair cell, hepatoblast, hepatocyte, hyalocyte, interstitial cell, juxtaglomerular cell, keratinocyte, keratocyte, lemmal cell, leukocyte, granulocyte, basophil, eosinophil, neutrophil, lymphoblast, B-lymphoblast, T-lymphoblast, lymphocyte, B-lymphocyte, T-lymphocyte, helper induced T-lymphocyte, Th1 T-lymphocyte, Th2 T-lymphocyte, natural killer cell, thymocyte, macrophage, Kupffer cell, alveolar macrophage, foam cell, histiocyte, luteal cell, lymphocytic stem cell, lymphoid cell, lymphoid stem cell, macroglial cell, mammotroph, mast cell, medulloblast, megakaryoblast, megakaryocyte, melanoblast, melanocyte, mesangial cell, mesothelial cell, metamyelocyte, monoblast, monocyte, mucous neck cell, muscle cell, cardiac muscle cell, skeletal muscle cell, smooth muscle cell, myelocyte, myeloid cell, myeloid stem cell, myoblast, myoepithelial cell, myofibrobast, neuroblast, neuroepithelial cell, neuron, odontoblast, osteoblast, osteoclast, osteocyte, oxyntic cell, parafollicular cell, paraluteal cell, peptic cell, pericyte, peripheral blood mononuclear cell, phaeochromocyte, phalangeal cell, pinealocyte, pituicyte, plasma cell, platelet, podocyte, proerythroblast, promonocyte, promyeloblast, promyelocyte, pronormoblast, reticulocyte, retinal pigment epithelial cell, retinoblast, small cell, somatotroph, stem cell, sustentacular cell, teloglial cell, or zymogenic cell.

A variety of disorders may be treated by employing the purified preparations of the methods of the present invention including, but not limited to, monogenic disorders, infectious diseases, acquired disorders, cancer, and the like. Exemplary monogenic disorders include ADA deficiency, cystic fibrosis, familial-hypercholesterolemia, hemophilia, chronic ganulomatous disease, Duchenne muscular dystrophy, Fanconi anemia, sickle-cell anemia, Gaucher's disease, Hunter syndrome, X-linked SCID, and the like. In another embodiment, the disorder treated involves one of the proteins listed below.

In another embodiment, the recombinant protein encoded by the purified preparation of an RNA, oligoribonucleotide, or polyribonucleotide of methods and compositions of the present invention is ecto-nucleoside triphosphate diphosphohydrolase. In another embodiment, the recombinant protein is erythropoietin (EPO).

In another embodiment, the encoded recombinant protein is mammalian proteins, such as an immunoglobulin, or a fragment thereof. In other embodiments, the encoded recombinant protein is a bacterial protein, a viral protein or a phage protein. In one embodiment, the encoded recombinant protein is streptokinase. In another embodiment, the encoded recombinant protein is a phage lysin.

In other embodiments, the encoded recombinant protein is at least one of ABCA4; ABCD3; ACADM; AGL; AGT; ALDH4A1; ALPL; AMPD1; APOA2; AVSD1; BRCD2; C1QA; C1QB; C1QG; CBA; C8B; CACNA1S; CCV; CD3Z; CDC2L1; CHML; CHS1; CIAS1; CLCNKB; CMD1A; CMH2; CMM; COL11A1; COL8A2; COL9A2; CPT2; CRB1; CSE; CSF3R; CTPA; CTSK; DBT; DIO1; DISC1; DPYD; EKV; ENO1; ENO1P; EPB41; EPHX1; F13B; F5; FCGR2A; FCGR2B; FCGR3A; FCHL; FH; FMO3; FMO4; FUCA1; FY; GALE; GBA; GFND; GJA8; GJB3; GLC3B; HF1; HMGCL; HPC1; HRD; HRPT2; HSD3B2; HSPG2; KCNQ4; KCS; KIF1B; LAMB3; LAMC2; LGMD1B; LMNA; LOR; MCKD1; MCL1; MPZ; MTHFR; MTR; MUTYH; MYOC; NB; NCF2; NEM1; NPHS2; NPPA; NRAS; NTRK1; OPTA2; PBX1; PCHC; PGD; PHA2A; PHGDH; PKLR; PKP1; PLA2G2A; PLOD; PPDX; PPT1; PRCC; PRG4; PSEN2; PTOS1; REN; RFXS; RHD; RMD1; RPE65; SCCD; SERPINC1; SJS1; SLC19A2; SLC2A1; SPG23; SPTA1; TAL1; TNFSF6; TNNT2; TPM3; TSHB; UMPK; UOX; UROD; USH2A; VMGLOM; VWS; WS2B; ABCB11; ABCG5; ABCG8; ACADL; ACP1; AGXT; AHHR; ALMS1; ALPP; ALS2; APOB; BDE; BDMR; BJS; BMPR2; CHRNA1; CMCWTD; CNGA3; COL3A1; COL4A3; COL4A4; COL6A3; CPS1; CRYGA; CRYGEP1; CYP1B1; CYP27A1; DBI; DES; DYSF; EDAR; EFEMP1; EIF2AK3; ERCC3; FSHR; GINGF; GLC1B; GPD2; GYPC; HADHA; HADHB; HOXD13; HPE2; IGKC; IHH; IRS1; ITGA6; KHK; KYNU; LCT; LHCGR; LSFC; MSH2; MSH6; NEB; NMTC; NPHP1; PAFAH1P1; PAX3; PAX8; PMS1; PNKD; PPH1; PROC; REG1A; SAG; SFTPB; SLC11A1; SLC3A1; SOS1; SPG4; SRD5A2; TCL4; TGFA; TMD; TPO; UGT1A@; UV24; WSS; XDH; ZAP70; ZFHX1B; ACAA1; AGS1; AGTR1; AHSG; AMT; ARMET; BBS3; BCHE; BCPM; BTD; CASR; CCR2; CCR5; CDL1; CMT2B; COL7A1; CP; CPO; CRV; CTNNB1; DEM; ETM1; FANCD2; FIH; FOXL2; GBE1; GLB1; GLC1C; GNAI2; GNAT1; GP9; GPX1; HGD; HRG; ITIH1; KNG; LPP; LRS1; MCCC1; MDS1; MHS4; MITF; MLH1; MYL3; MYMY; OPA1; P2RY12; PBXP1; PCCB; POU1F1; PPARG; PROS1; PTHR1; RCA1; RHO; SCA7; SCLC1; SCN5A; SI; SLC25A20; SLC2A2; TF; TGFBR2; THPO; THRB; TKT; TM4SF1; TRH; LIMPS; UQCRC1; USH3A; VHL; WS2A; XPC; ZNF35; ADH1B; ADH1C; AFP; AGA; AIH2; ALB; ASMD; BFHD; CNGA1; CRBM; DCK; DSPP; DTDP2; ELONG; ENAM; ETFDH; EVC; F11; FABP2; FGA; FGB; FGFR3; FGG; FSHMD1A; GC; GNPTA; GNRHR; GYPA; HCA; HCL2; HD; HTN3; HVBS6; IDUA; IF; JPD; KIT; KLKB1; LQT4; MANBA; MLLT2; MSX1; MTP; NR3C2; PBT; PDE6B; PEE1; PITX2; PKD2; QDPR; SGCB; SLC25A4; SNCA; SOD3; STATH; TAPVR1; TYS; WBS2; WFS1; WHCR; ADAMTS2; ADRB2; AMCN; AP3B1; APC; ARSB; B4GALT7; BHR1; C6; C7; CCAL2; CKN1; CMDJ; CRHBP; CSF1R; DHFR; DIAPH1; DTR; EOS; EPD; ERVR; F12; FBN2; GDNF; GHR; GLRA1; GM2A; HEXB; HSD17B4; ITGA2; KFS; LGMD1A; LOX; LTC4S; MAN2A1; MCC; MCCC2; MSH3; MSX2; NR3C1; PCSK1; PDE6A; PFBI; RASA1; SCZD1; SDHA; SGCD; SLC22A5; SLC26A2; SLC6A3; SM1; SMA@; SMN1; SMN2; SPINKS; TCOF1; TELAB1; TGFBI; ALDH5A1; ARG1; AS; ASSP2; BCKDHB; BF; C2; C4A; CDKN1A; COL10A1; COL11A2; CYP21A2; DYX2; EJM1; ELOVL4; EPM2A; ESR1; EYA4; F13A1; FANCE; GCLC; GJA1; GLYS1; GMPR; GSE; HCR; HFE; HLA-A; HLA-DPB1; HLA-DRA; HPFH; ICS1; IDDM1; IFNGR1; IGAD1; IGF2R; ISCW; LAMA2; LAP; LCA5; LPA; MCDR1; MOCS1; MUT; MYB; NEU1; NKS1; NYS2; OA3; ODDD; OFC1; PARK2; PBCA; PBCRA1; PDB1; PEX3; PEX6; PEX7; PKHD1; PLA2G7; PLG; POLH; PPAC; PSORS1; PUJO; RCD1; RDS; RHAG; RP14; RUNX2; RWS; SCA1; SCZD3; SIASD; SOD2; ST8; TAP1; TAP2; TFAP2B; TNDM; TNF; TPBG; TPMT; TULP1; WISP3; AASS; ABCB1; ABCB4; ACHE; AQP1; ASL; ASNS; AUTS1; BPGM; BRAF; C7orf2; CACNA2D1; CCM1; CD36; CFTR; CHORDOMA; CLCN1; CMH6; CMT2D; COL1A2; CRS; CYMD; DFNA5; DLD; DYT11; EEC1; ELN; ETV1; FKBP6; GCK; GNRHR; GHS; GLI3; GPDS1; GUSB; HLXB9; HOXA13; HPFH2; HRX; IAB; IMMP2L; KCNH2; LAMB1; LEP; MET; NCF1; NM; OGDH; OPN1SW; PEX1; PGAM2; PMS2; PON1; PPP1R3A; PRSS1; PTC; PTPN12; RP10; RP9; SERPINE1; SGCE; SHFM1; SHH; SLC26A3; SLC26A4; SLOS; SMAD1; TBXAS1; TWIST; ZWS1; ACHM3; ADRB3; ANK1; CA1; CA2; CCAL1; CLN8; CMT4A; CNGB3; COH1; CPP; CRH; CYP11B1; CYP11B2; DECR1; DPYS; DURS1; EBS1; ECA1; EGI; EXT1; EYA1; FGFR1; GNRH1; GSR; GULOP; HR; KCNQ3; KFM; KWE; LGCR; LPL; MCPH1; MOS; MYC; NAT1; NAT2; NBS1; PLAT; PLEC1; PRKDC; PXMP3; RP1; SCZD6; SFTPC; SGM1; SPG5A; STAR; TG; TRPS1; TTPA; VMD1; WRN; ABCA1; ABL1; ABO; ADAMTS13; AK1; ALAD; ALDH1A1; ALDOB; AMBP; AMCD1; ASS; BDMF; BSCL; C5; CDKN2A; CHAC; CLA1; CMD1B; COL5A1; CRAT; DBH; DNAI1; DYS; DYT1; ENG; FANCC; FBP1; FCMD; FRDA; GALT; GLDC; GNE; GSM1; GSN; HSD17B3; HSN1; IBM2; INVS; JBTS1; LALL; LCCS1; LCCS; LGMD2H; LMX1B; MLLT3; MROS; MSSE; NOTCH1; ORM1; PAPPA; PIP5K1B; PTCH; PTGS1; RLN1; RLN2; RMRP; ROR2; RPD1; SARDH; SPTLC1; STOM; TDFA; TEK; TMC1; TRIM32; TSC1; TYRP1; XPA; CACNB2; COL17A1; CUBN; CXCL12; CYP17; CYP2C19; CYP2C9; EGR2; EMX2; ERCC6; FGFR2; HK1; HPS1; IL2RA; LGI1; LIPA; MAT1A; MBL2; MKI67; MXI1; NODAL; OAT; OATL3; PAX2; PCBD; PEO1; PHYH; PNLIP; PSAP; PTEN; RBP4; RDPA; RET; SFTPA1; SFTPD; SHFM3; SIAL; THC2; TLX1; TNFRSF6; UFS; UROS; AA; ABCC8; ACAT1; ALX4; AMPD3; ANC; APOA1; APOA4; APOC3; ATM; BSCL2; BWS; CALCA; CAT; CCND1; CD3E; CD3G; CD59; CDKN1C; CLN2; CNTF; CPT1A; CTSC; DDB1; DDB2; DHCR7; DLAT; DRD4; ECB2; ED4; EVR1; EXT2; F2; FSHB; FTH1; G6PT1; G6PT2; GIF; HBB; HBBP1; HBD; HBE1; HBG1; HBG2; HMBS; HND; HOMG2; HRAS; HVBS1; IDDM2; IGER; INS; JBS; KCNJ11; KCNJ1; KCNQ1; LDHA; LRPS; MEN1; MLL; MYBPC3; MYO7A; NNO1; OPPG; OPTB1; PAX6; PC; PDX1; PGL2; PGR; PORC; PTH; PTS; PVRL1; PYGM; RAG1; RAG2; ROM1; RRAS2; SAA1; SCA5; SCZD2; SDHD; SERPING1; SMPD1; TCIRG1; TCL2; TECTA; TH; TREH; TSG101; TYR; USH1C; VMD2; VRNI; WT1; WT2; ZNF145; A2M; AAAS; ACADS; ACLS; ACVRL1; ALDH2; AMHR2; AOM; AQP2; ATD; ATP2A2; BDC; C1R; CD4; CDK4; CNA1; COL2A1; CYP27B1; DRPLA; ENUR2; FEOM1; FGF23; FPF; GNB3; GNS; HAL; HBP1; HMGA2; HMN2; HPD; IGF1; KCNA1; KERA; KRAS2; KRT1; KRT2A; KRT3; KRT4; KRT5; KRT6A; KRT6B; KRTHB6; LDHB; LYZ; MGCT; MPE; MVK; MYL2; OAP; PAH; PPKB; PRB3; PTPN11; PXR1; RLS; RSN; SAS; SAX1; SCA2; SCNN1A; SMAL; SPPM; SPSMA; TBX3; TBX5; TCF1; TPI1; TSC3; ULR; VDR; VWF; ATP7B; BRCA2; BRCD1; CLN5; CPB2; ED2; EDNRB; ENUR1;

ERCC5; F10; F7; GJB2; GJB6; IPF1; MBS1; MCOR; NYS4; PCCA; RB1; RHOK; SCZD7; SGCG; SLC10A2; SLC25A15; STARP1; ZNF198; ACHM1; ARVD1; BCH; CTAA1; DAD1; DFNB5; EML1; GALC; GCH1; IBGC1; IGH@; IGHC group; IGHG1; IGHM; IGHR; IV; LTBP2; MCOP; MJD; MNG1; MPD1; MPS3C; MYH6; MYH7; NP; NPC2; PABPN1; PSEN1; PYGL; RPGRIP1; SERPINA1; SERPINA3; SERPINA6; SLC7A7; SPG3A; SPTB; TCL1A; TGM1; TITF1; TMIP; TRA@; TSHR; USH1A; VP; ACCPN; AHO2; ANCR; B2M; BBS4; BLM; CAPN3; CDAN1; CDAN3; CLN6; CMH3; CYP19; CYP1A1; CYP1A2; DYX1; EPB42; ETFA; EYCL3; FAH; FBN1; FES; HCVS; HEXA; IVD; LCS1; LIPC; MYOSA; OCA2; OTSC1; PWCR; RLBP1; SLC12A1; SPG6; TPM1; UBE3A; WMS; ABCC6; ALDOA; APRT; ATP2A1; BBS2; CARD15; CATM; CDH1; CETP; CHST6; CLN3; CREBBP; CTH; CTM; CYBA; CYLD; DHS; DNASE1; DPEP1; ERCC4; FANCA; GALNS; GAN; HAGH; HBA1; HBA2; HBHR; HBQ1; HBZ; HBZP; HP; HSD11B2; IL4R; LIPB; MC1R; MEFV; MHC2TA; MLYCD; MMVP1; PHKB; PHKG2; PKD1; PKDTS; PMM2; PXE; SALL1; SCA4; SCNN1B; SCNN1G; SLC12A3; TAT; TSC2; VDI; WT3; ABR; ACACA; ACADVL; ACE; ALDH3A2; APOH; ASPA; AXIN2; BCL5; BHD; BLMH; BRCA1; CACD; CCA1; CCZS; CHRNB1; CHRNE; CMT1A; COL1A1; CORDS; CTNS; EPX; ERBB2; G6PC; GAA; GALK1; GCGR; GFAP; GH1; GH2; GP1BA; GPSC; GUCY2D; ITGA2B; ITGB3; ITGB4; KRT10; KRT12; KRT13; KRT14; KRT14L1; KRT14L2; KRT14L3; KRT16; KRT16L1; KRT16L2; KRT17; KRT9; MAPT; MDB; MDCR; MGI; MHS2; MKS1; MPO; MYO15A; NAGLU; NAPB; NF1; NME1; P4HB; PAFAH1B1; PECAM1; PEX12; PHB; PMP22; PRKAR1A; PRKCA; PRKWNK4; PRP8; PRPF8; PTLAH; RARA; RCV1; RMSA1; RP17; RSS; SCN4A; SERPINF2; SGCA; SGSH; SHBG; SLC2A4; SLC4A1; SLC6A4; SMCR; SOST; SOX9; SSTR2; SYM1; SYNS1; TCF2; THRA; TIMP2; TOC; TOP2A; TP53; TRIM37; VBCH; ATP8B1; BCL2; CNSN; CORD1; CYBS; DCC; F5F8D; FECH; FEO; LAMA3; LCFS2; MADH4; MAFD1; MC2R; MCL; MYP2; NPC1; SPPK; TGFBRE; TGIF; TTR; AD2; AMH; APOC2; APOE; ATHS; BAX; BCKDHA; BCL3; BFIC; C3; CACNA1A; CCO; CEACAM5; COMP; CRX; DBA; DDU; DFNA4; DLL3; DM1; DMWD; E11S; ELA2; EPOR; ERCC2; ETFB; EXT3; EYCL1; FTL; FUT1; FUT2; FUT6; GAMT; GCDH; GPI; GUSM; HB 1; HCL1; HHC2; HHC3; ICAM3; INSR; JAK3; KLK3; LDLR; LHB; LIG1; LOH19CR1; LYL1; MAN2B1; MCOLN1; MDRV; MLLT1; NOTCH3; NPHS1; OFC3; OPA3; PEPD; PRPF31; PRTN3; PRX; PSG1; PVR; RYR1; SLC5A5; SLC7A9; STK11; TBXA2R; TGFB1; TNNI3; TYROBP; ADA; AHCY; AVP; CDAN2; CDPD1; CHED1; CHED2; CHRNA4; CST3; EDN3; EEGV1; FTLL1; GDF5; GNAS; GSS; HNF4A; JAG1; KCNQ2; MKKS; NBIA1; PCK1; PI3; PPCD; PPGB; PRNP; THBD; TOP1; AIRE; APP; CBS; COL6A1; COL6A2; CSTB; DCR; DSCR1; FPDMM; HLCS; HPE1; ITGB2; KCNE1; KNO; PRSS7; RUNX1; SOD1; TAM; ADSL; ARSA; BCR; CECR; CHEK2; COMT; CRYBB2; CSF2RB; CTHM; CYP2D6; CYP2D7P1; DGCR; DIA1; EWSR1; GGT1; MGCR; MN1; NAGA; NF2; OGS2; PDGFB; PPARA; PRODH; SCO2; SCZD4; SERPIND1; SLC5A1; SOX10; TCN2; TIMP3; TST; VCF; ABCD1; ACTL1; ADFN; AGMX2; AHDS; AIC; AIED; AIH3; ALAS2; AMCD; AMELX; ANOP1; AR; ARAF1; ARSC2; ARSE; ARTS; ARX; ASAT; ASSPS; ATP7A; ATRX; AVPR2; BFLS; BGN; BTK; BZX; C1HR; CACNA1F; CALB3; CBBM; CCT; CDR1; CFNS; CGF1; CHM; CHR39C; CIDX; CLA2; CLCNS; CLS; CMTX2; CMTX3; CND; COD1; COD2; COL4A5; COL4A6; CPX; CVD1; CYBB; DCX; DFN2; DFN4; DFN6; DHOF; DIAPH2; DKC1; DMD; DSS; DYT3; EBM; EBP; ED1; ELK1; EMD; EVR2; F8; F9; FCP1; FDPSLS; FGD1; FGS1; FMR1; FMR2; G6PD; GABRA3; GATA1; GDI1; GDXY; GJB1; GK; GLA; GPC3; GRPR; GTD; GUST; HMS1; HPRT1; HPT; HTC2; HTR2C; HYR; IDS; IHG1; IL2RG; INDX; IP1; IP2; JMS; KAL1; KFSD; L1CAM; LAMP2; MAA; MAFD2; MAOA; MAOB; MCF2; MCS; MEAX; MECP2; MF4; MGC1; MICS; MIDI; MLLT7; MLS; MRSD; MRX14; MRX1; MRX20; MRX2; MRX3; MRX40; MRXA; MSD; MTM1; MYCL2; MYP1; NDP; NHS; NPHL1; NROB1; NSX; NYS1; NYX; OA1; OASD; OCRL; ODT1; OFD1; OPA2; OPD1; OPEM; OPN1LW; OPN1MW; OTC; P3; PDHA1; PDR; PFC; PFKFB1; PGK1; PGK1P1; PGS; PHEX; PHKA1; PHKA2; PHP; PIGA; PLP1; POF1; POLA; POU3F4; PPMX; PRD; PRPS1; PRPS2; PRS; RCCP2; RENBP; RENS1; RP2; RP6; RPGR; RPS4X; RPS6KA3; RS1; S11; SDYS; SEDL; SERPINA7; SH2D1A; SHFM2; SLC25A5; SMAX2; SRPX; SRS; STS; SYN1; SYP; TAF1; TAZ; TBX22; TDD; TFE3; THAS; THC; TIMM8A; TIMP1; TKCR; TNFSF5; UBE1; UBE2A; WAS; WSN; WTS; WWS; XIC; XIST; XK; XM; XS; ZFX; ZIC3; ZNF261; ZNF41; ZNF6; AMELY; ASSP6; AZF1; AZF2; DAZ; GCY; RPS4Y; SMCY; SRY; ZFY; ABAT; AEZ; AFA; AFD1; ASAHl; ASD1; ASMT; CCAT; CECR9; CEPA; CLA3; CLN4; CSF2RA; CTS1; DF; DIH1; DWS; DYT2; DYT4; EBR3; ECT; EEF1A1L14; EYCL2; FANCB; GCSH; GCSL; GIP; GTS; HHG; HMI; HOAC; HOKPP2; HRPT1; HSD3B3; HTC1; HV1S; ICHQ; ICR1; ICR5; IL3RA; KAL2; KMS; KRT18; KSS; LCAT; LHON; LIMM; MANBB; MCPH2; MEB; MELAS; MIC2; MPFD; MS; MSS; MTATP6; MTCO1; MTCO3; MTCYB; MTND1; MTND2; MTND4; MTND5; MTND6; MTRNR1; MTRNR2; MTTE; MTTG; MTTI; MTTK; MTTL1; MTTL2; MTTN; MTTP; MTTS1; NAMSD; OCD1; OPD2; PCK2; PCLD; PCOS1; PFKM; PKD3; PRCA1; PRO1; PROP1; RBS; RFXAP; RP; SHOX; SLC25A6; SPGSB; STO; SUOX; THM; or TTD.

In another embodiment, the present invention provides a method for treating anemia in a subject, comprising contacting a cell of the subject with a purified preparation of an in vitro-synthesized RNA molecule, the in vitro-synthesized RNA encoding erythropoietin, thereby treating anemia in a subject. In another embodiment, the in vitro-synthesized RNA further comprises a pseudouridine or a modified nucleoside. In another embodiment, the cell is a subcutaneous tissue cell. In another embodiment, the cell is a lung cell. In another embodiment, the cell is a fibroblast. In another embodiment, the cell is a lymphocyte. In another embodiment, the cell is a smooth muscle cell. In another embodiment, the cell is any other type of cell known in the art.

In another embodiment, the present invention provides a method for treating a vasospasm in a subject, comprising contacting a cell of the subject with a purified preparation of an in vitro-synthesized RNA molecule, the in vitro-synthesized RNA encoding inducible nitric oxide synthase (iNOS), thereby treating a vasospasm in a subject.

In another embodiment, the present invention provides a method for improving a survival rate of a cell in a subject, comprising contacting the cell with a purified preparation of an in vitro-synthesized RNA molecule, the in vitro-synthesized RNA encoding a heat shock protein, thereby improving a survival rate of a cell in a subject. In another embodiment, the cell whose survival rate is improved is an ischemic cell. In another embodiment, the cell is not ischemic. In another embodiment, the cell has been exposed to an ischemic environment. In another embodiment, the cell has been exposed to an environmental stress.

In another embodiment, the present invention provides a method for decreasing an incidence of restenosis of a blood vessel following a procedure that enlarges the blood vessel, comprising contacting a cell of the blood vessel with a purified preparation of an in vitro-synthesized RNA molecule, the in vitro-synthesized RNA encoding a heat shock protein, thereby decreasing an incidence of restenosis in a subject.

In another embodiment, the present invention provides a method for increasing a hair growth from a hair follicle is a scalp of a subject, comprising contacting a cell of the scalp with a purified preparation of an in vitro-synthesized RNA molecule, the in vitro-synthesized RNA encoding a telomerase or an immunosuppressive protein, thereby increasing a hair growth from a hair follicle. In another embodiment, the immunosuppressive protein is a-melanocyte-stimulating hormone (α-MSH). In another embodiment, the immunosuppressive protein is transforming growth factor-β1 (TGF-β1). In another embodiment, the immunosuppressive protein is insulin-like growth factor-I (IGF-I). In another embodiment, the immunosuppressive protein is any other immunosuppressive protein known in the art.

In another embodiment, the present invention provides a method of inducing expression of an enzyme with antioxidant activity in a cell, comprising contacting the cell with a purified preparation of an in vitro-synthesized RNA molecule, the in vitro-synthesized RNA encoding the enzyme, thereby inducing expression of an enzyme with antioxidant activity in a cell. In another embodiment, the enzyme is catalase. In another embodiment, the enzyme is glutathione peroxidase. In another embodiment, the enzyme is phospholipid hydroperoxide glutathione peroxidase. In another embodiment, the enzyme is superoxide dismutase-1. In another embodiment, the enzyme is superoxide dismutase-2. In another embodiment, the enzyme is any other enzyme with antioxidant activity that is known in the art. In another embodiment, the present invention provides a method for treating cystic fibrosis in a subject, comprising contacting a cell of the subject with a purified preparation of an in vitro-synthesized RNA molecule, the in vitro-synthesized RNA encoding Cystic Fibrosis Transmembrane Conductance Regulator (CFTR), thereby treating cystic fibrosis in a subject.

In another embodiment, the present invention provides a method for treating damage to heart muscle with a purified, nucleoside modified mRNA encoding VEGF-A. In another embodiment, the present invention provides a method for treating an X-linked agammaglobulinemia in a subject, comprising contacting a cell of the subject with a purified preparation of an in vitro-synthesized RNA molecule, the in vitro-synthesized RNA encoding a Bruton's tyrosine kinase, thereby treating an X-linked agammaglobulinemia.

In another embodiment, the present invention provides a method for treating an adenosine deaminase severe combined immunodeficiency (ADA SCID) in a subject, comprising contacting a cell of the subject with a purified preparation of a purified preparation of an in vitro-synthesized RNA molecule, the in vitro-synthesized RNA encoding an ADA, thereby treating an ADA SCID.

In another embodiment, the present invention provides a method for reducing immune responsiveness of the skin and improve skin pathology, comprising contacting a cell of the subject with a purified preparation of an in vitro-synthesized RNA molecule, the in vitro-synthesized RNA encoding an ecto-nucleoside triphosphate diphosphohydrolase, thereby reducing immune responsiveness of the skin and improve skin pathology.

In another embodiment, the purified preparation of an RNA or ribonucleotide of the present invention is encapsulated in a nanoparticle. Methods for nanoparticle packaging are well known in the art, and are described, for example, in Bose et al., (2004, J. Virol. 78:8146); Dong et al., (2005, Biomaterials 26:6068); Lobenberg et al., (1998, J Drug Target 5:171); Sakuma et al., (1999, Int J Pharm 177:161. 1999); Virovic et al., (2005, Expert Opin Drug Deliv 2:707); and Zimmermann et al., (2001, Eur J Pharm Biopharm 52:203).

Various embodiments of dosage ranges of compounds of the present invention can be used in methods of the present invention. In one embodiment, the dosage is in the range of 1-10 μg/day. In another embodiment, the dosage is 2-10 μg/day. In another embodiment, the dosage is 3-10 μg/day. In another embodiment, the dosage is 5-10 μg/day. In another embodiment, the dosage is 2-20 μg/day. In another embodiment, the dosage is 3-20 μg/day. In another embodiment, the dosage is 5-20 μg/day. In another embodiment, the dosage is 10-20 μg/day. In another embodiment, the dosage is 3-40 μg/day. In another embodiment, the dosage is 5-40 μg/day. In another embodiment, the dosage is 10-40 μg/day. In another embodiment, the dosage is 20-40 μg/day. In another embodiment, the dosage is 5-50 μg/day. In another embodiment, the dosage is 10-50 μg/day. In another embodiment, the dosage is 20-50 μg/day. In one embodiment, the dosage is 1-100 μg/day. In another embodiment, the dosage is 2-100 μg/day. In another embodiment, the dosage is 3-100 μg/day. In another embodiment, the dosage is 5-100 μg/day. In another embodiment the dosage is 10-100 μg/day. In another embodiment the dosage is 20-100 μg/day. In another embodiment the dosage is 40-100 μg/day. In another embodiment the dosage is 60-100 μg/day.

In another embodiment, the dosage is 0.1 μg/day. In another embodiment, the dosage is 0.2 μg/day. In another embodiment, the dosage is 0.3 μg/day. In another embodiment, the dosage is 0.5 μg/day. In another embodiment, the dosage is 1 μg/day. In another embodiment, the dosage is 2 mg/day. In another embodiment, the dosage is 3 μg/day. In another embodiment, the dosage is 5 μg/day. In another embodiment, the dosage is 10 μg/day. In another embodiment, the dosage is 15 μg/day. In another embodiment, the dosage is 20 μg/day. In another embodiment, the dosage is 30 μg/day. In another embodiment, the dosage is 40 μg/day. In another embodiment, the dosage is 60 μg/day. In another embodiment, the dosage is 80 μg/day. In another embodiment, the dosage is 100 μg/day.

In another embodiment, the dosage is 10 μg/dose. In another embodiment, the dosage is 20 μg/dose. In another embodiment, the dosage is 30 μg/dose. In another embodiment, the dosage is 40 μg/dose. In another embodiment, the dosage is 60 μg/dose. In another embodiment, the dosage is 80 μg/dose. In another embodiment, the dosage is 100 μg/dose. In another embodiment, the dosage is 150 μg/dose. In another embodiment, the dosage is 200 μg/dose. In another embodiment, the dosage is 300 μg/dose. In another embodiment, the dosage is 400 μg/dose. In another embodiment, the dosage is 600 μg/dose. In another embodiment, the dosage is 800 μg/dose. In another embodiment, the dosage is 1000 μg/dose. In another embodiment, the dosage is 1.5 mg/dose. In another embodiment, the dosage is 2 mg/dose. In another embodiment, the dosage is 3 mg/dose. In another embodiment, the dosage is 5 mg/dose. In another embodiment, the dosage is 10 mg/dose. In another embodiment, the dosage is 15 mg/dose. In another embodiment, the dosage is 20 mg/dose. In another embodiment, the dosage is 30 mg/dose. In another embodiment, the dosage is 50 mg/dose. In another embodiment, the dosage is 80 mg/dose. In another embodiment, the dosage is 100 mg/dose.

In another embodiment, the dosage is 10-20 µg/dose. In another embodiment, the dosage is 20-30 µg/dose. In another embodiment, the dosage is 20-40 µg/dose. In another embodiment, the dosage is 30-60 µg/dose. In another embodiment, the dosage is 40-80 µg/dose. In another embodiment, the dosage is 50-100 µg/dose. In another embodiment, the dosage is 50-150 µg/dose. In another embodiment, the dosage is 100-200 µg/dose. In another embodiment, the dosage is 200-300 µg/dose. In another embodiment, the dosage is 300-400 µg/dose. In another embodiment, the dosage is 400-600 µg/dose. In another embodiment, the dosage is 500-800 µg/dose. In another embodiment, the dosage is 800-1000 µg/dose. In another embodiment, the dosage is 1000-1500 µg/dose. In another embodiment, the dosage is 1500-2000 µg/dose. In another embodiment, the dosage is 2-3 mg/dose. In another embodiment, the dosage is 2-5 mg/dose. In another embodiment, the dosage is 2-10 mg/dose. In another embodiment, the dosage is 2-20 mg/dose. In another embodiment, the dosage is 2-30 mg/dose. In another embodiment, the dosage is 2-50 mg/dose. In another embodiment, the dosage is 2-80 mg/dose. In another embodiment, the dosage is 2-100 mg/dose. In another embodiment, the dosage is 3-10 mg/dose. In another embodiment, the dosage is 3-20 mg/dose. In another embodiment, the dosage is 3-30 mg/dose. In another embodiment, the dosage is 3-50 mg/dose. In another embodiment, the dosage is 3-80 mg/dose. In another embodiment, the dosage is 3-100 mg/dose. In another embodiment, the dosage is 5-10 mg/dose. In another embodiment, the dosage is 5-20 mg/dose. In another embodiment, the dosage is 5-30 mg/dose. In another embodiment, the dosage is 5-50 mg/dose. In another embodiment, the dosage is 5-80 mg/dose. In another embodiment, the dosage is 5-100 mg/dose. In another embodiment, the dosage is 10-20 mg/dose. In another embodiment, the dosage is 10-30 mg/dose. In another embodiment, the dosage is 10-50 mg/dose. In another embodiment, the dosage is 10-80 mg/dose. In another embodiment, the dosage is 10-100 mg/dose.

In another embodiment, the dosage is a daily dose. In another embodiment, the dosage is a weekly dose. In another embodiment, the dosage is a monthly dose. In another embodiment, the dosage is an annual dose. In another embodiment, the dose is one is a series of a defined number of doses. In another embodiment, the dose is a one-time dose. As described below, in another embodiment, an advantage of RNA, oligoribonucleotide, or polyribonucleotide molecules of the present invention is their greater potency, enabling the use of smaller doses.

In another embodiment, the present invention provides a method for producing a recombinant protein, comprising contacting an in vitro translation apparatus with an in vitro-synthesized oligoribonucleotide, the in vitro-synthesized oligoribonucleotide comprising a 1-methyl-pseudouridine or a modified nucleoside, thereby producing a recombinant protein.

In another embodiment, the present invention provides a method for producing a recombinant protein, comprising contacting an in vitro translation apparatus with an in vitro-transcribed RNA of the present invention, the in vitro-transcribed RNA comprising a pseudouridine or a modified nucleoside, thereby producing a recombinant protein.

In another embodiment, the present invention provides an in vitro transcription apparatus, comprising: an unmodified nucleotide, a nucleotide containing a pseudouridine or a modified nucleoside, and a polymerase. In another embodiment, the present invention provides an in vitro transcription kit, comprising: an unmodified nucleotide, a nucleotide containing a pseudouridine or a modified nucleoside, a polymerase and instructional material. As used herein, an "instructional material" includes a publication, a recording, a diagram, or any other medium of expression, which can be used to communicate the usefulness of a compound, composition, or method of the invention in a kit. The instructional material of the kit of the invention can, for example, be affixed to a container which contains the identified compound, composition, or method of the invention or be shipped together with a container, which contains the identified compound, composition, or method of the invention. Alternatively, the instructional material can be shipped separately from the container with the intention that the instructional material and the compound, composition, or method of the invention be used cooperatively by the recipient.

In another embodiment, the present invention provides a method of reducing the immunogenicity of an oligoribonucleotide or RNA molecule, the method comprising the step of replacing a nucleotide of the oligoribonucleotide or RNA with a modified nucleotide that contains a modified nucleoside or a 1-methyl-pseudouridine, and purifying the preparation of modified oligoribonucleotide or RNA molecule, thereby reducing the immunogenicity of an oligoribonucleotide or RNA molecule.

In another embodiment, the present invention provides a method of reducing the immunogenicity of a gene-therapy vector comprising a polyribonucleotide or RNA molecule, the method comprising the step of replacing a nucleotide of the polyribonucleotide or RNA with a modified nucleotide that contains a modified nucleoside or a 1-methyl-pseudouridine, and purifying the preparation of modified oligoribonucleotide or RNA molecule, thereby reducing the immunogenicity of a gene-therapy vector.

In another embodiment, the present invention provides a method of enhancing in vitro translation from an oligoribonucleotide or RNA molecule, the method comprising the step of replacing a nucleotide of the oligoribonucleotide or RNA with a modified nucleotide that contains a modified nucleoside or a 1-methyl-pseudouridine, and purifying the preparation of modified oligoribonucleotide or RNA molecule, thereby enhancing in vitro translation from an oligoribonucleotide or RNA molecule.

In another embodiment, the present invention provides a method of enhancing in vivo translation from a gene-therapy vector comprising a polyribonucleotide or RNA molecule, the method comprising the step of replacing a nucleotide of the polyribonucleotide or RNA with a modified nucleotide that contains a modified nucleoside or a 1-methyl-pseudouridine, and purifying the preparation of modified oligoribonucleotide or RNA molecule, thereby enhancing in vivo translation from a gene-therapy vector.

In another embodiment, the present invention provides a method of increasing efficiency of delivery of a recombinant protein by a gene therapy vector comprising a polyribonucleotide or RNA molecule, the method comprising the step of replacing a nucleotide of the polyribonucleotide or RNA with a modified nucleotide that contains a modified nucleoside or a 1-methyl-pseudouridine, and purifying the preparation of modified oligoribonucleotide or RNA molecule, thereby increasing efficiency of delivery of a recombinant protein by a gene therapy vector.

In another embodiment, the present invention provides a method of increasing in vivo stability of gene therapy vector comprising a polyribonucleotide or RNA molecule, the method comprising the step of replacing a nucleotide of the polyribonucleotide or RNA with a modified nucleotide that contains a modified nucleoside or a 1-methyl-pseudouridine, and purifying the preparation of modified oligoribonucleotide or RNA molecule, thereby increasing in vivo stability of gene therapy vector.

In another embodiment, the present invention provides a method of reducing the ability of an RNA to stimulate signaling by TLR3, comprising modifying a nucleoside of the RNA by a method of the present invention, and purifying the preparation of modified RNA. In another embodiment, the present invention provides a method of reducing the ability of an RNA to stimulate signaling by TLR7, comprising modifying a nucleoside of the RNA by a method of the present invention, and purifying the preparation of modified RNA. In another embodiment, the present invention provides a method of reducing the ability of an RNA to stimulate signaling by TLR8, comprising modifying a nucleoside of the RNA by a method of the present invention, and purifying the preparation of modified RNA.

In another embodiment, the present invention provides a method of reducing the ability of an RNA to stimulate signaling by PKR, comprising modifying a nucleoside of the RNA by a method of the present invention, and purifying the preparation of modified RNA. In another embodiment, the present invention provides a method of reducing the ability of an RNA to stimulate signaling by oligoadenylates synthase, comprising modifying a nucleoside of the RNA by a method of the present invention, and purifying the preparation of modified RNA. In another embodiment, the present invention provides a method of reducing the ability of an RNA to stimulate signaling by RIG-I, comprising modifying a nucleoside of the RNA by a method of the present invention, and purifying the preparation of modified RNA. In another embodiment, the present invention provides a method of reducing the ability of an RNA to stimulate signaling by MDA5, comprising modifying a nucleoside of the RNA by a method of the present invention, and purifying the preparation of modified RNA. In another embodiment, the present invention provides a method of reducing the ability of an RNA to stimulate signaling by NOD2, comprising modifying a nucleoside of the RNA by a method of the present invention, and purifying the preparation of modified RNA. In another embodiment, the present invention provides a method of reducing the ability of an RNA to stimulate signaling by DDX41, comprising modifying a nucleoside of the RNA by a method of the present invention, and purifying the preparation of modified RNA. In another embodiment, the present invention provides a method of reducing the ability of an RNA to stimulate signaling by NALP3, comprising modifying a nucleoside of the RNA by a method of the present invention, and purifying the preparation of modified RNA.

In another embodiment, all the inter-nucleotide linkages in the RNA, oligoribonucleotide, or polyribonucleotide are phosphodiester. In another embodiment, the inter-nucleotide linkages are predominantly phosphodiester. In another embodiment, most of the inter-nucleotide linkages are phosphorothioate. In another embodiment, most the inter-nucleotide linkages are phosphodiester.

In another embodiment, the percentage of the inter-nucleotide linkages that are phosphodiester is above 50%. In another embodiment, the percentage is above 10%. In another embodiment, the percentage is above 15%. In another embodiment, the percentage is above 20%. In another embodiment, the percentage is above 25%. In another embodiment, the percentage is above 30%. In another embodiment, the percentage is above 35%. In another embodiment, the percentage is above 40%. In another embodiment, the percentage is above 45%. In another embodiment, the percentage is above 55%. In another embodiment, the percentage is above 60%. In another embodiment, the percentage is above 65%. In another embodiment, the percentage is above 70%. In another embodiment, the percentage is above 75%. In another embodiment, the percentage is above 80%. In another embodiment, the percentage is above 85%. In another embodiment, the percentage is above 90%. In another embodiment, the percentage is above 95%.

In another embodiment, a method of the present invention comprises increasing the number, percentage, or frequency of modified nucleosides in the RNA to decrease immunogenicity or increase efficiency of translation. As provided herein, the number of modified residues in an RNA, oligoribonucleotide, or polyribonucleotide determines, in another embodiment, the magnitude of the effects observed in the present invention.

In another embodiment, the present invention provides a method for introducing a recombinant protein into a cell of a subject, comprising contacting the subject with a purified preparation of an in vitro-transcribed RNA encoding the recombinant protein, the in vitro-transcribed RNA further comprising a modified nucleoside, thereby introducing a recombinant protein into a cell of a subject.

In another embodiment, the present invention provides a method for decreasing TNF-α production in response to a gene therapy vector in a subject, comprising the step of engineering the vector to contain a pseudouridine or a modified nucleoside base, and purifying the preparation of the gene therapy vector, thereby decreasing TNF-α production in response to a gene therapy vector in a subject.

In another embodiment, the present invention provides a method for decreasing IFN-α production in response to a gene therapy vector in a subject, comprising the step of engineering the vector to contain a pseudouridine or a modified nucleoside base, and purifying the preparation of the gene therapy vector, thereby decreasing IFN-α production in response to a gene therapy vector in a subject.

In another embodiment, the present invention provides a method for decreasing IFN-β production in response to a gene therapy vector in a subject, comprising the step of engineering the vector to contain a pseudouridine or a modified nucleoside base, and purifying the preparation of the gene therapy vector, thereby decreasing IFN-β production in response to a gene therapy vector in a subject.

In another embodiment, the present invention provides a method for decreasing IL-12 production in response to a gene therapy vector in a subject, comprising the step of engineering the vector to contain a pseudouridine or a modified nucleoside base, and purifying the preparation of the gene therapy vector, thereby decreasing IL-12 production in response to a gene therapy vector in a subject.

In another embodiment, the present invention provides a method of reducing an immunogenicity of a gene therapy vector, comprising introducing a modified nucleoside into the gene therapy vector, and purifying the preparation of the gene therapy vector, thereby reducing an immunogenicity of a gene therapy vector.

In another embodiment, an advantage of the purified preparation of an RNA, oligoribonucleotide, and polyribonucleotide of the present invention is that RNA does not incorporate to the genome (as opposed to DNA-based vectors). In another embodiment, an advantage is that translation of RNA, and therefore appearance of the encoded product, is instant. In another embodiment, an advantage is that the amount of protein generated from the mRNA can be regulated by delivering more or less RNA. In another embodiment, an advantage is that repeated delivery of unmodified RNA could induce autoimmune reactions. In another embodiment, an advantage is that reducing or removing contaminants from the RNA preparation reduces or eliminates immunogenicity of the purified RNA preparation as compared with the unpurified RNA preparation. In another embodiment, an advantage is that reducing or removing dsRNA from the RNA preparation reduces or eliminates immunogenicity of the purified RNA preparation as compared with the unpurified RNA preparation.

In another embodiment, an advantage is lack of immunogenicity, enabling repeated delivery without generation of inflammatory cytokines.

In another embodiment, the present invention provides a kit comprising a reagent utilized in performing a method of the present invention. In another embodiment, the present invention provides a kit comprising a composition, tool, instructional material, or instrument of the present invention.

In another embodiment, a treatment protocol of the present invention is therapeutic. In another embodiment, the protocol is prophylactic.

In one embodiment, the phrase "contacting a cell" or "contacting a population" refers to a method of exposure, which can be direct or indirect. In one method such contact comprises direct injection of the cell through any means well known in the art, such as microinjection. In another embodiment, supply to the cell is indirect, such as via provision in a culture medium that surrounds the cell, or administration to a subject, or via any route known in the art. In another embodiment, the term "contacting" means that the purified preparation of the present invention is introduced into a subject receiving treatment, and the purified preparation is allowed to come in contact with the cell in vivo.

In various embodiments, the purified preparations of the compositions of the present invention can be administered to a subject by any method known to a person skilled in the art, such as parenterally, paracancerally, transmucosally, transdermally, intramuscularly, intravenously, intra-dermally, subcutaneously, intra-peritonealy, intra-ventricularly, intracranially, intra-vaginally or intra-tumorally.

In another embodiment, the purified preparations of the methods and compositions of the present invention, the compositions are administered orally, and are thus formulated in a form suitable for oral administration, i.e., as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelating capsule.

In other embodiments, the pharmaceutical compositions are administered by intravenous, intra-arterial, or intramuscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical compositions are administered topically to body surfaces and are thus formulated in a form suitable for topical administration. Suitable topical formulations include gels, ointments, creams, lotions, drops and the like. For topical administration, the compositions or their physiologically tolerated derivatives are prepared and applied as solutions, suspensions, or emulsions in a physiologically acceptable diluent with or without a pharmaceutical carrier.

In another embodiment, the composition is administered as a suppository, for example a rectal suppository or a urethral suppository. In another embodiment, the pharmaceutical composition is administered by subcutaneous implantation of a pellet. In another embodiment, the pellet provides for controlled release of agent over a period of time.

In another embodiment, the active compound is delivered in a vesicle, e.g. a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989)).

As used herein "pharmaceutically acceptable carriers or diluents" are well known to those skilled in the art. The carrier or diluent may be may be, in various embodiments, a solid carrier or diluent for solid formulations, a liquid carrier or diluent for liquid formulations, or mixtures thereof.

In another embodiment, solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In another embodiment, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCI, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents(e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In another embodiment, the pharmaceutical compositions provided herein are controlled-release compositions, i.e. compositions in which the compound is released over a period of time after administration. Controlled- or sustained-release compositions include formulation in lipophilic depots (e.g. fatty acids, waxes, oils). In another embodiment, the composition is an immediate-release composition, i.e., a composition in which the entire compound is released immediately after administration.

In another embodiment, molecules of the present invention are modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds. Such modifications also increase, in another embodiment, the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

An active component is, in another embodiment, formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

EXPERIMENTAL EXAMPLE

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Purification and Purity Assessment of RNA Molecules Synthesized with Modified Nucleosides As described herein, the purification of mRNA results in up to a 5,000-fold increase in translation and protein production, in primary cells and in vivo compared to unpurified in vitro transcribed RNA through the removal of contaminants, such as dsRNA and other RNAs that do not encode the sequence of interest that activate RNA sensors that inhibit protein translation directly or indirectly. In addition, when such purified RNA contains certain modified nucleosides, it can also ablate activation of innate immune RNA sensors resulting in a highly translatable, low-immunogenic RNA. Described herein are three methods, both quantitative and qualitative, to measure the purification of mRNA preparations.

The materials and methods are now described.
In Vitro-Transcribed RNA

RNA containing modified nucleosides was synthesized essentially as described in U.S. Pat. No. 8,278,036. RNA containing modified nucleosides was purified using high-performance liquid chromatography (HPLC) and/or RNase III treatment.

RNA was purified by HPLC (Akta Purifier, GE Healthcare) using a column matrix of alkylated nonporous polystyrene-divinylbenzene copolymer microspheres (2.1 µm) (21 mm×100 mm column). Buffer A contained 0.1 M triethylammonium acetate (TEAA), pH=7.0 and Buffer B contained 0.1 M TEAA, pH=7.0 and 25% acetonitrile (Transgenomics). Columns were equilibrated with 38% Buffer B, loaded with RNA, and run with a single or 2 linear gradients to 55 or 65% Buffer B over 20-30 minutes at 5 ml/minute. RNA analyses were performed with the same column matrix and buffer system using a 7.8 mm×50 mm column at 1.0 ml/min.

RNA content from desired fractions was concentrated and desalted using Amicon Ultra-15 centrifugal filter units (30K membrane) (Millipore) by successive centrifugation at 4,000×g for 10 min (4° C.) in a Sorvall ST16R centrifuge (Thermo Scientific) and dilution with nuclease free water. The RNA was recovered by overnight precipitation at −20° C. in NaOAc (0.3 M, pH 5.5), isopropanol (1 volume) (Fisher) and glycogen (3 µl) (Roche).

RNase III purification was performed by making the RNA buffer 66 mM Na acetate, pH=7.5 to a volume of 100 µl and adding 0.001 units of RNase III and incubating at 37° C. for 60 minutes. RNA was purified away from enzyme and salt using LiCl precipitation.

Dot Blot

A major contaminant found in modified nucleoside RNA preparations is dsRNA. Binding of dsRNA-specific mAb J2 occurs even when the dsRNA contains modified nucleosides, e.g., 1-methyl-pseudouridine, pseudouridine and/or 5-methylcytidine, while binding of the other dsRNA-specific mAb K1 is reduced when dsRNA contains such modifications (Kariko, et al., 2011, Nucleic Acids Res 39:e142).

RNA (200 ng) was blotted onto super charged Nytran, dried, blocked with 5% non-fat dried milk in TBS-T buffer (50 mM Tris-HCl, 150 mM NaCl, 0.05% Tween-20, pH 7.4), and incubated with dsRNA-specific mAb J2 or K1 (English & Scientific Consulting) for 60 min. Membranes were washed six times with TBS-T and reacted with HRP-conjugated donkey anti-mouse Ig (Jackson Immunology), washed six times and detected with ECL Plus Western blot detection reagent (Amersham).

Images were captured on a Fujifilm LAS1000 digital imaging system. dsRNA (25 ng) used as a positive control was derived from sense and antisense strands of T7TS UTR sequence (328 bp). Blots were reprobed with $^{32}$P-labeled DNA complementary to the 3'-UTR of the RNA to document the presence of RNA. The assay can be further quantitated by varying the amount of RNA blotted onto the membrane and creating a standard curve of known double-stranded RNA using increasing amounts blotted onto membranes. This allows the quantitation of the amount of dsRNA in a known quantity of mRNA.

Northern Blot

The mRNA of interest is derived from a specific region of the plasmid bounded by a T7 promoter and a sequence corresponding to a poly(A) tail. RNA contaminants can be derived from any region of the plasmid containing the RNA sequence of interest. To identify contaminants, the in vitro transcribed mRNA is analyzed by Northern blot using probes derived from all of the regions of the plasmid excluding the coding sequence of interest. The mRNA of interest and signal from contaminating RNA can be quantitated and represented as the percent impurity.

Northern blot analyses were performed with in vitro synthesized RNA. The RNA pellet was reconstituted in 25 µl of nuclease-free water (Promega) and stored at −20° C. RNA samples (5 µl) containing 1 µg of RNA were denatured and then separated in a 1.4% denaturing agarose, 0.22 M formaldehyde gel that was submerged into morpholinepropanesulfonic acid (MOPS)-EDTA-sodium acetate buffer (Sigma) supplemented with formaldehyde (0.22 M). RNA was transferred to NYTRAN SuperCharge filters (Schleicher and Schuell, Keene, N.H.) and UV cross-linked. The filters were prehybridized at 68° C. for 1 h in MiracleHyb (Stratagene, La Jolla, Calif.). To probe the Northern blots, 50 ng of DNA probe corresponding to the coding sequence, UTRs, or regions of the plasmid used to make the RNA was labeled with Redivue [α-32P]dCTP (Amersham, Arlington Heights, Ill.) with a random prime-labeling kit (Boehringer Mannheim). The filters were hybridized at 68° C. for 20 h with MiracleHyb containing the labeled and denatured probe. The filters were washed and exposed to Kodak film with an intensifier screen at −70° C. for 2 to 72 h.

HPLC Analysis

Although the Northern blot method accurately quantitates contaminating RNA and allows the quantitation of the increase in purity by HPLC, it does not measure RNA contaminants that are derived from the coding sequence of interest on the plasmid, derived by aberrant start or stop sites or transcription from the opposite strand. These contaminants, as well as all other contaminants, can be accurately quantitated by HPLC analysis using the same parameters as used for purification. HPLC purification results in mRNA that ranges between 98% and 99.9% pure starting with in vitro transcribed RNA that is typically 70-93% pure. Thus, the HPLC method is the very accurate and predictive of RNA purity.

Dendritic Cell Activation

The addition of RNA to human primary DCs and the measurement of the resultant inflammatory cytokine protein or mRNA is a very sensitive measure that the mRNA has been purified to its optimum. This assay cannot quantitate the purity of the RNA, but it is the most sensitive and accurate at determining whether the mRNA is purified to its optimal amount. The optimal level of purity needed varies for each mRNA coding sequence and cannot be predicted. The DC activation assay is used to discern whether an RNA preparation is optimally purified.

Leukophoresis samples were obtained from HIV-uninfected volunteers through an IRB-approved protocol. Peripheral blood mononuclear cells were purified by Ficoll-Hypaque density gradient purification. DCs were produced by adhering monocytes to plastic 6-well plates and removing unbound cells. GM-CSF (50 µg/ml) and IL-4 (100 µg/ml, R & D Systems) were added. The resulting immature DCs were used between 6 and 9 days after the initial culture of monocytes.

Lipofectin (Invitrogen, Carlsbad, CA) and mRNA were complexed in phosphate buffer that has been shown to enhance transfection in vitro and in vivo. To assemble a 50-µl complex of RNA-lipofectin, first 0.4 µl potassium phosphate buffer (0.4 mol/l, pH 6.2) containing 10 µg/µl bovine serum albumin (Sigma, St. Louis, MO) was added to 6.7 µl DMEM, then 0.8 µl lipofectin was mixed in and the sample was incubated for 10 minutes. In a separate tube, RNA was added to DMEM to a final volume of 3.3 µl. Diluted RNA was added to the lipofectin mix and incubated for 10 minutes. Finally, the RNA-lipofectin complex was further diluted by adding 38.8 µl DMEM. Fifty microliter of such a complex was used to transfect cells present in 1 well of a 96-well plate. Complexing of RNA to TransIT mRNA (Minis Bio) was performed according to the manufacturer combining RNA (0.1 mg) with TransIT mRNA (0.3 ml) and boost (0.2 ml) reagents in 17 µl of serum free medium, which was then added to DCs. Culture supernatants were collected at 24 h and analyzed for inflammatory cytokines (TNF-α, IFN-α, IL-6, and others) by ELISA assay. Cellular RNA was obtained 6 hrs after stimulation and analyzed by Northern blot, as described above with the following changes. Total RNA was isolated from cells with guanidinium thiocyanate (Master Blaster; Bio-Rad, Hercules, Calif). To enhance the RNA yield, 70 µg of glycogen (Boehringer Mannheim, Indianapolis, Ind.) was added as carrier, and the precipitation was performed in siliconized tubes at −20° C. overnight. Probes were derived from plasmids and were specific for the coding regions of human IFN-α13, IFN-β (Open Biosystems), TNF-α, or GAPDH (ATCC).

The results of this example are now described.

Figure 1B:
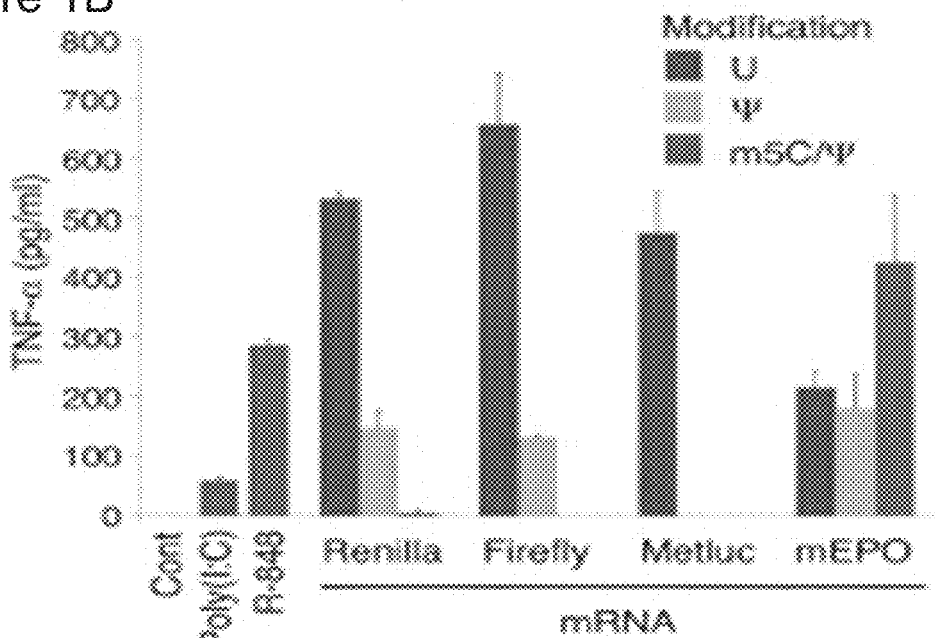
Figure 1C:
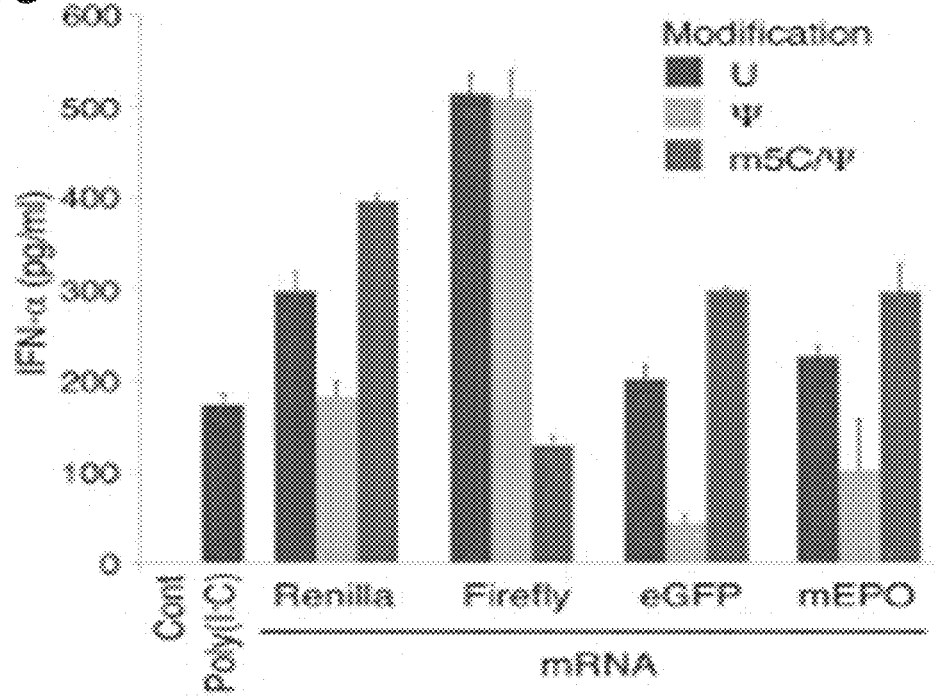

Experiments were performed that demonstrate that in vitro transcribed RNA is immunogenic and contains dsRNA contaminants. 200 ng of in vitro transcripts encoding mEPO and containing the indicated modified nucleosides were blotted and analyzed with K1 and J2 dsRNA-specific mAbs. The dsRNA positive control contained a 328 bp long dsRNA (25 ng) (FIG. 1A). DCs were treated with Lipofectin-complexed Renilla luciferase (T7TSRenA$_{30}$), firefly and Metridia luciferases (T7TSLucA$_{30}$, T7TSMetlucA$_{30}$), and mEPO (TEVmEPOA$_{51}$) mRNAs. TNF-α levels were measured in the supernatants at 24 h (FIG. 1B). DCs were treated with TransIT-complexed in vitro transcripts encoding Renilla and firefly luciferases (T7TSRenA$_{30}$, T7TSLucA$_{30}$), eGFP (TEVeGFPA$_{51}$) and mEPO (TEVmEPOA$_{51}$). IFN-α levels were measured in the supernatants at 24 h. Error bars are standard error of the mean. Data shown is from one experiment that is representative of greater than 20 experiments using many different coding sequence mRNAs (FIG. 1C).

Figure 2:
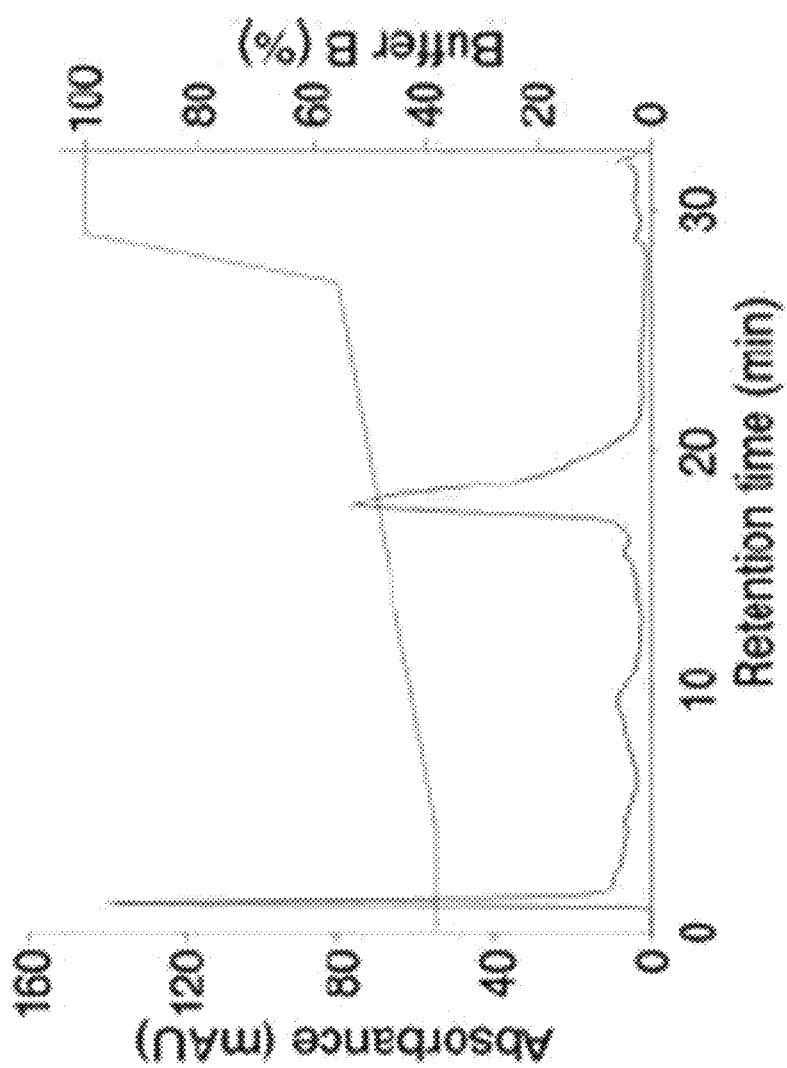
FIG. 2 depicts a chromatogram of Ψ-modified TEVeGFPA$_n$ mRNA. HPLC purification of RNA identifies contaminants eluting before and after the expected product. RNA was applied to the HPLC column and eluted using a linear gradient of Buffer B (0.1 M TEAA, pH 7.0, 25% acetonitrile) in Buffer A (0.1 M TEAA, pH 7.0). The gradient spanned 38-55% Buffer B over 22 min (red line). Absorbance at 260 nm was analyzed (black line), which demonstrated the expected sized RNA as well as smaller and larger RNA species. Data shown is from one experiment that is representative of over 200.

HPLC purification of Ψ-modified TEVeGFPA$_n$ mRNA identified contaminants eluting before and after the expected product (FIG. 2). RNA was applied to the HPLC column and eluted using a linear gradient of Buffer B (0.1 M TEAA, pH 7.0, 25% acetonitrile) in Buffer A (0.1 M TEAA, pH 7.0). The gradient spanned 38-55% Buffer B over 22 min (red line). Absorbance at 260 nm was analyzed (black line), which demonstrated the expected sized RNA as well as smaller and larger RNA species. Data shown is from one experiment that is representative of over 200.

HPLC purification of in vitro-transcribed nucleoside modified mRNA was found to remove dsRNA contaminants and eliminate immunogenicity. 200 ng of RNA encoding the indicated protein and containing the indicated modified nucleosides with or without HPLC-purification were blotted and analyzed with the J2 dsRNA-specific mAb (FIG. 3A). 200 ng of RNA encoding the indicated protein and containing Ψ-modifications with or without HPLC-purification were blotted and analyzed with the J2 dsRNA-specific mAb. Blots were reprobed with a 32P-labeled probe for the 3' UTR of the RNAs to control for amount of RNA analyzed (FIG. 3B). DCs were treated with TEVRenA$_{51}$ RNA containing the indicated nucleoside modifications with or without HPLC purification and complexed to Lipofectin. TNF-α levels were measured in the supernatants at 24 hr. Differences in the effect of nucleoside modification on immunogenicity of Renilla encoding mRNA compared to FIG. 1B is likely due to donor variation and differences in UTRs of the RNAs (FIG. 3C). DCs were treated with TEVLucA$_{51}$ RNA containing the indicated nucleoside modifications with or without HPLC purification and complexed to TransIT. IFN-α levels were measured in the supernatants at 24 hr. Error bars are standard error of the mean. Data shown is from one experiment that is representative of 3 or more (FIG. 3D).

Figure 4A:
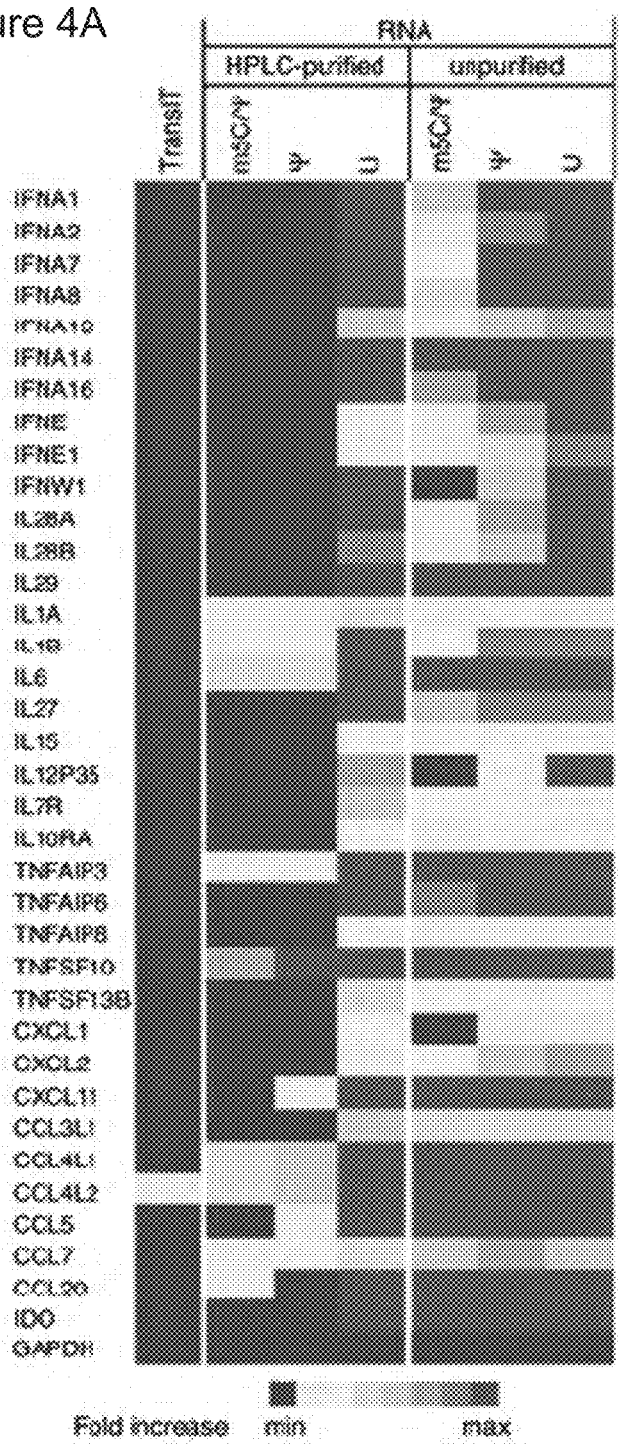
FIGS. 4A and 4B, depicts the results of analyses demonstrating that HPLC purification of in vitro transcribed nucleoside-modified mRNA eliminates activation of genes associated with RNA sensor activation.
Figure 4B:
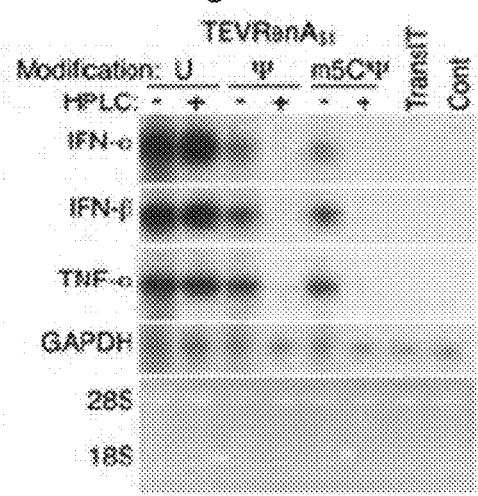

HPLC purification of in vitro transcribed nucleoside-modified mRNA was found to eliminate activation of genes associated with RNA sensor activation. Heat map representing changes in expression of genes activated by RNA sensors were derived from microarray analyses of DCs treated for 6 hr with TransIT alone or transit-complexed TEVRenA$_{51}$ RNA with the indicated modifications with or without HPLC purification. RNA from medium treated cells was used as the baseline for comparison (FIG. 4A). Northern blot of RNA from DCs treated with medium or TransIT alone or TransIT-complexed TEVRenA$_{51}$ RNA with the indicated modifications with or without HPLC purification and probed for IFN-α, IFN-β, TNF-α, and GAPDH mRNAs (FIG. 4B).

HPLC purification of in vitro transcribed mRNA was found to enhance translation. 293T (FIG. 5A) and human DCs (FIG. 5B-5C) were transfected with TransIT (FIG. 5A, 5C) or Lipofectin (FIG. 5B) complexed TEVRenA$_{51}$ or TEVmEPOA$_{51}$ mRNA with the indicated modifications with or without HPLC purification and analyzed for Renilla luciferase activity or levels of supernatant-associated mEPO protein at 24 hr. (FIG. 5D) Human DCs were transfected with Ψ-modified TEVeGFPA$_n$ mRNA with or without HPLC purification (0.1 µg/well) complexed with Lipofectin or TransIT and analyzed 24 hr later. Error bars are standard error of the mean. Data shown is from one experiment that is representative of 3 or more.

Figure 6A:
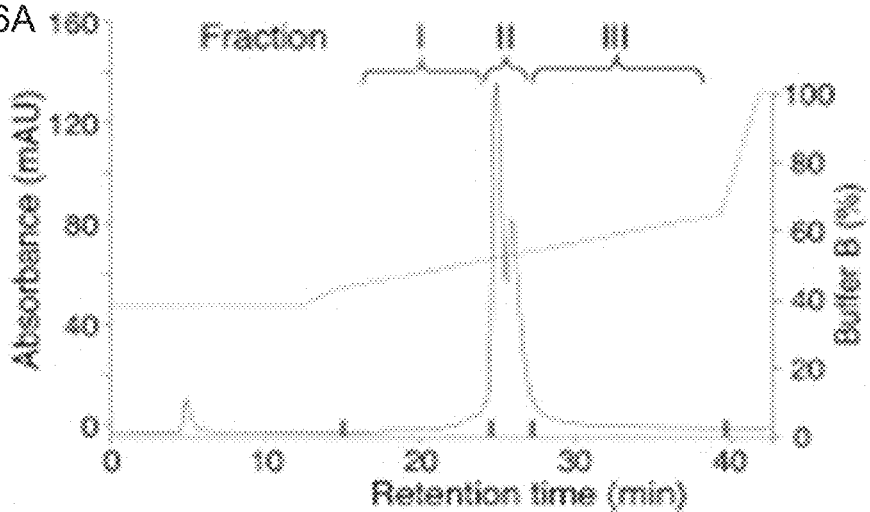
FIGS. 6A-6C, depicts the results of analyses showing that RNA contaminants are removed by HPLC purification.
Figure 6B:
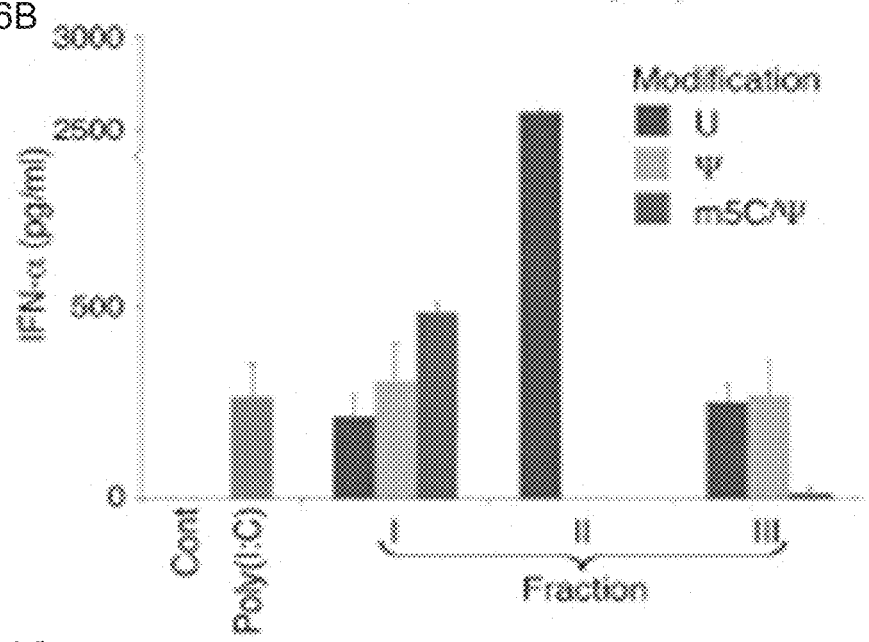
Figure 6C:
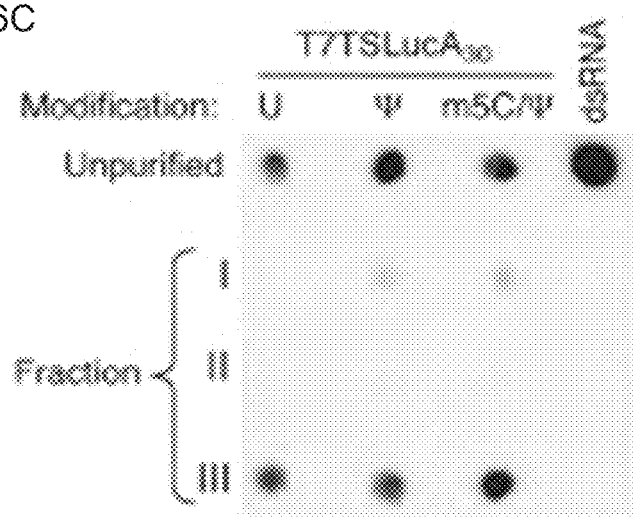

HPLC purification was found to remove RNA contaminants. (FIG. 6A) One hundred µg of Ψ-modified T7TSLucA$_{30}$ RNA was applied to the HPLC column and 3 fractions were collected, all RNAs eluting before the main transcription product (I), the expected RNA (II), and all RNAs eluting after the main transcription product (III). The gradient began at 38% Buffer B and increased to 43% Buffer B over 2.5 min and then spanned 43% to 65% Buffer B over 22 min. Unmodified and m5C/Ψ-modified T7TSLucA$_{30}$ RNA had similar fractions obtained. (FIG. 6B) The RNAs from each fraction were complexed to TransIT and added to DCs and IFN-α in the supernatant was measured 24 hr later. Error bars are standard error of the mean. (FIG. 6C) 200 ng of RNA from the 3 fractions and the starting unpurified RNA were blotted and analyzed with the J2 dsRNA-specific mAb.

Figure 7:
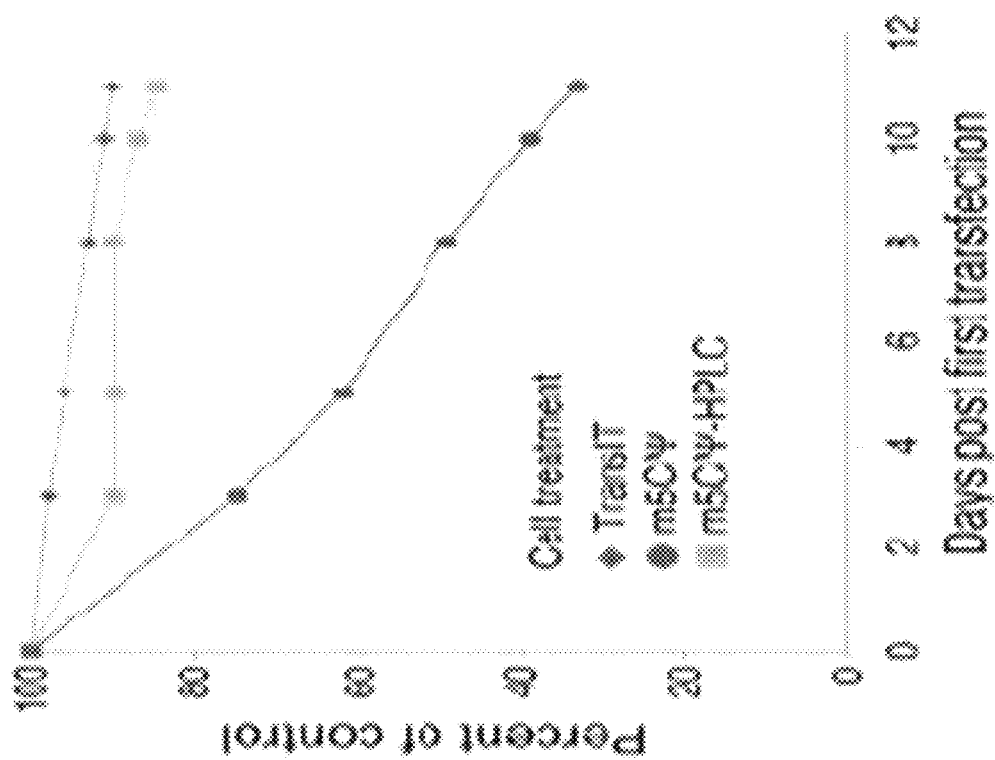
FIG. 7 depicts the results of an exemplary experiment demonstrating that daily transfection with HPLC-purified m5C/Ψ-modified mRNA does not reduce cell proliferation. Primary keratinocytes were transfected daily with TransIT alone or m5C/Ψ-modified RNA encoding Renilla luciferase with or without HPLC-purification complexed with TransIT. Every 2-3 days, cultures were split and equal numbers of cells for each condition were plated. Total cell numbers for each condition were divided by the total cell number in untreated cells to calculate the percent of control proliferation.

Daily transfection with HPLC-purified m5C/Ψ-modified mRNA does not reduce cell proliferation (FIG. 7). Primary keratinocytes were transfected daily with TransIT alone or m5C/Ψ-modified RNA encoding Renilla luciferase with or without HPLC-purification complexed with TransIT. Every 2-3 days, cultures were split and equal numbers of cells for each condition were plated. Total cell numbers for each condition were divided by the total cell number in untreated cells to calculate the percent of control proliferation.

RNA contaminants were found to be removed by treatment with RNase III (FIG. 8). One hundred µg of U, Ψ, m5C/Ψ, or 1-Me-Ψ-modified TEV-ren-A51 RNA was treated with 0.001 units of bacterial RNase III for 60 minutes at 37° C. in 66 mM acetate buffer, pH=7.5. Similar results were obtained with ranges of RNase III from about 0.001 to about 0.1 units, with treatment times ranging from about 15 to about 120 minutes, and concentrations of acetate buffer ranging from about 33 to about 200 mM and pHs ranging from about 7.5 to about 8.0. After precipitation, washing and resuspension in water, 200 ng of RNA was analyzed for binding by the dsRNA-specific mAb J2 (FIG. 8A) or 300 ng of RNA was complexed to TransIT and added to primary human monocyte derived dendritic cells (FIG. 8B). After 24 hrs, supernatant was analyzed for interferon (IFN)-α.

Multiple exemplary RNA preparations have been produced and have been found to contain contaminants, including dsRNA contaminants, and they have been purified using the methods described elsewhere herein to remove immunogenicity. Exemplary RNA preparations that have been produced and purified using the methods described elsewhere herein include bacterial Cas9, Firefly luciferase, Metridia luciferase, Renilla luciferase, green fluorescent protein, enhanced green fluorescent protein, mouse CD40L, mouse 4-1BBL, mouse CD70, HIV envelope, HIV gag, HIV protease, mouse OX40L, mouse CD80, mouse Wnt10b, 6RHU3-SL, D2-1BiMAB-S, 6RHU3-SL, SIINFEKL, gp70AH5mini, murine tyrosinase, influenza HA, TLR3, TLR4, mouse GM-CSF, human, macaque, and mouse EPO, beta-gal, NGF-beta-endorphin, VRC01 monoclonal antibody, human iNos, dsRed, Semliki forest virus, Zinc finger nucleases, mouse SFTPD-Myc/DDK, mouse and human CD39, mouse and human CD73, mouse and human DNaseI, mouse and human RNaseI, mouse and human telomerase, Klf4, Lin28, cMyc, Nanog, Sox2, Oct4, IL18, CCL5, IL1Beta, TNFa, FCAR, 7SL, Let7a2, premir16, and b-lactamase.

TABLE 1

| RNA Number | Backbone | Coding Sequence | Purity Before HPLC | Purity After HPLC | Enhanced Translation in 293 T (log) | Enhanced Translation in DC (log) | Enhanced Translation in Animal (log) | Immunogenicity DCs after HPLC | Binding by double stranded RNA-specific mAb after HPLC |
|---|---|---|---|---|---|---|---|---|---|
| 6181 + 6190 | pppTEV | VRC01-light-A101-Y | 76.39% | ~96-99.5% | 0.95 | | >3 | 0 | 0 |
| 6182 + 6191 | pppTEV | VRC01-heavy-2PA-light-A101-Y | 92.66% | ~96-99.5% | 1.1 | | | 0 | 0 |
| 6198 | pppTEV | VRC01-heavy-2PA-light-A101-Y | 93.70% | ~96-99.5% | 1.1 | | | 0 | 0 |
| 6210 | pppTEV | dsRED-A101-Y | 93.18% | ~96-99.5% | | | | 0 | 0 |
| 6192 | NrcapT7TS | bGAL-Y | 91.99% | ~96-99.5% | | | | 0 | 0 |
| 6166 | pppTEV | IR3A HIV envelope-A101-Y | 83.19% | ~96-99.5% | | | >3 | 0 | 0 |
| 6183 | pppTEV | NGFs-betaendorphine-A101-Y | 87.69% | ~96-99.5% | | | | 0 | 0 |
| 6183 | pppTEV | NGFs-betaendorphine-A101-Y | 88.02% | ~96-99.5% | | | | 0 | 0 |
| 5649 | pppTEV | oPL-A51-Y | 80.88% | ~96-99.5% | | | | 0 | 0 |
| 6088 | pppTEV | eGFP-A101-Y | 87.01% | ~96-99.5% | 0.65 | 1.8 | >3 | 0 | 0 |
| 6096 | pppTEV | gag-A101-Y | 92.33% | ~96-99.5% | 0.72 | 2.2 | >3 | 0 | 0 |
| 6091 | pppTEV | CD40L-A101-Y | 73.22% | ~96-99.5% | | 1.9 | >3 | 0 | 0 |
| 6092 | pppTEV | caTLR4-A101-Y | 80.80% | ~96-99.5% | | 1.7 | >3 | 0 | 0 |
| 6093 | pppTEV | caTLR3-A101-Y | 78.50% | ~96-99.5% | | 1.75 | >3 | 0 | 0 |
| 6063 | pppTEV | huTertRT-A101-Y | 82.37% | ~96-99.5% | | | | 0 | 0 |
| 6049 | pppTEV | CD39-Flagtag-A101-Y | 89.23% | ~96-99.5% | | | >3 | 0 | 0 |
| 6050 | pppTEV | CD73-Flagtag-A101-Y | 80.43% | ~96-99.5% | | | >3 | 0 | 0 |
| 6051 | pppTEV | DNaseI-Flagtag-A101-Y | 88.74% | ~96-99.5% | | | >3 | 0 | 0 |
| 6052 | pppTEV | mRNaseI-Flagtag-A101-Y | 90.47% | ~96-99.5% | | | >3 | 0 | 0 |
| 6022 | Nrcap-T7TS | huiNOS-A30-Y | 85.68% | ~96-99.5% | | | | 0 | 0 |
| 5807 | pppTEV | Niv-M-A101-Y | 87.00% | ~96-99.5% | | | | 0 | 0 |
| 5893 | | cap1-Oct4-Y | 83.66% | ~96-99.5% | | | | 0 | 0 |
| 5892 | | cap1-Sox2-Y | 81.63% | ~96-99.5% | | | | 0 | 0 |
| 5891 | | cap1-Nanog-Y | 87.20% | ~96-99.5% | | | | 0 | 0 |
| 5890 | | cap1-cMyc-T58A-Y | 80.25% | ~96-99.5% | | | | 0 | 0 |
| 5889 | | cap1-Lin28-Y | 86.82% | ~96-99.5% | | | | 0 | 0 |
| 5888 | | cap1-Klf4-Y | 88.84% | ~96-99.5% | | | | 0 | 0 |
| 5867 | pppTEV | luc-A101-Y | 64.59% | ~96-99.5% | 0.75 | 1.9 | 3.5 | 0 | 0 |
| 5841 | pppTEV | gag-eGFP-A101-Y | 87.31% | ~96-99.5% | 0.87 | 2.4 | >3 | 0 | 0 |
| 5705 | cap1-TEV | HIV envelope-A51-Y | 82.85% | ~96-99.5% | | 1.4 | >3 | 0 | 0 |
| 5706 | cap1-TEV | HIV envelope D/R-A51-Y | 82.34% | ~96-99.5% | | 1.45 | >3 | 0 | 0 |
| 5717 | ppp-TEV | omEPO-A51-Y | 87.50% | ~96-99.5% | 0.98 | 2.1 | 3.15 | 0 | 0 |
| 5647 | cap1-TEV | pontellaFP-A101-Y | 84.17% | ~96-99.5% | | 2.2 | | 0 | 0 |
| 5648 | cap1-TEV | luc-tmtomato-A101-Y | 84.38% | ~96-99.5% | | | | 0 | 0 |
| 5649 | pppTEV | oPL-A51-Y | 88.43% | ~96-99.5% | | | | 0 | 0 |
| 5560 | cap1-TEV | NivM-GFP-A101-Y | 85.85% | ~96-99.5% | | | | 0 | 0 |
| 5519 | cap1-TEV | beta-lactamasestop-A101-Y | 75.47% | ~96-99.5% | | | | 0 | 0 |
| 5515 | cap1-TEV | ren-A101-Y | 83.47% | ~96-99.5% | 0.52 | 2.3 | | 0 | 0 |
| 5424 | cap1-TEV | eIF4E-A101-Y | 79.73% | ~96-99.5% | | | | 0 | 0 |
| 5340 | cap1-TEV | huAntiTripsinA101-m5C/Y | 89.18% | ~96-99.5% | | | | 0 | 0 |
| 5286 with Cap1 | cap1-TEV2 | eRRhEPO-A101-m5C/Y | 76.23% | ~96-99.5% | 0.88 | 2.3 | >3 | 0 | 0 |

What is claimed is:

1. A method of preparing a purified preparation of RNA comprising at least one modified nucleoside selected from the group consisting of a 1-methyl-pseudouridine, m5C, m5U, m6A, s2U, Ψ, and 2'-O-methyl-U comprising the steps of:
   a. producing a preparation of messenger RNA comprising at least one modified nucleoside;
   b. subjecting the preparation of messenger RNA comprising at least one modified nucleoside to enzymatic digestion with 0.001 units of at least one enzyme selected from the group consisting of RNase III, RNase V1, Dicer, and Chipper; and
   c. isolating the purified preparation of messenger RNA comprising at least one modified nucleoside.

2. A method of inducing a mammalian cell to produce a protein of interest, the method comprising the step of contacting the mammalian cell with the purified preparation of RNA prepared by the method of claim 1, thereby inducing the mammalian cell to produce the protein of interest.

3. A method of preparing a purified preparation of RNA comprising at least one modified nucleoside selected from the group consisting of a 1-methyl-pseudouridine, m5C, m5U, m6A, s2U, Ψ, and 2'-O-methyl-U comprising the steps of:
   a. producing a preparation of messenger RNA comprising at least one modified nucleoside;
   b. subjecting the preparation of messenger RNA comprising at least one modified nucleoside to liquid chromatography using a linear gradient of 38% Buffer B (0.1 M triethylammonium acetate, 25% acetonitrile, pH 7.0) to 55% Buffer B in Buffer A (0.1 M triethylammonium acetate, pH 7.0) over 22 minutes; and
   c. isolating the purified preparation of messenger RNA comprising at least one modified nucleoside.

4. A method of inducing a mammalian cell to produce a protein of interest, the method comprising the step of contacting the mammalian cell with the purified preparation of RNA prepared by the method of claim 3, thereby inducing the mammalian cell to produce the protein of interest.

5. A method of preparing a purified preparation of RNA comprising at least one modified nucleoside comprising the steps of:
   a. producing a preparation of messenger RNA comprising at least one modified nucleoside;
   b. subjecting the preparation of messenger RNA comprising at least one modified nucleoside to at least one purification process selected from the group consisting of enzyme digestion with 0.001 units of at least one enzyme selected from the group consisting of RNase III, RNase V1, Dicer, and Chipper and liquid chromatography using a linear gradient of 38% Buffer B (0.1 M triethylammonium acetate, 25% acetonitrile, pH 7.0) to 55% Buffer B in Buffer A (0.1 M triethylammonium acetate, pH 7.0) over 22 minutes; and
   c. isolating the purified preparation of messenger RNA comprising at least one modified nucleoside.

6. The method of claim 5, wherein the at least one modified nucleoside is selected from the group consisting of 1-methyl-pseudouridine, m5C, m5U, m6A, s2U, Ψ, and 2'-O-methyl-U.

7. A method of inducing a mammalian cell to produce a protein of interest, the method comprising the step of contacting the mammalian cell with the purified preparation of RNA prepared by the method of claim 5, thereby inducing the mammalian cell to produce the protein of interest.

* * * * *